US009237990B2

(12) United States Patent
Abuelyaman et al.

(10) Patent No.: US 9,237,990 B2
(45) Date of Patent: *Jan. 19, 2016

(54) POLYMERIZABLE ISOCYANURATE MONOMERS AND DENTAL COMPOSITIONS

(75) Inventors: Ahmed S. Abuelyaman, Woodbury, MN (US); Sumita B. Mitra, West Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 310 days.

This patent is subject to a terminal disclaimer.

(21) Appl. No.: 13/575,686

(22) PCT Filed: Mar. 8, 2011

(86) PCT No.: PCT/US2011/027523
§ 371 (c)(1),
(2), (4) Date: Jul. 27, 2012

(87) PCT Pub. No.: WO2011/126647
PCT Pub. Date: Oct. 13, 2011

(65) Prior Publication Data
US 2013/0012614 A1 Jan. 10, 2013

Related U.S. Application Data

(60) Provisional application No. 61/319,534, filed on Mar. 31, 2010.

(51) Int. Cl.
*A61K 6/083* (2006.01)
*C08L 33/08* (2006.01)
*C08L 33/10* (2006.01)
*C08L 35/02* (2006.01)
*C08L 37/00* (2006.01)
*C08L 39/04* (2006.01)
*C08L 101/00* (2006.01)
*C08F 20/12* (2006.01)
*C08F 20/38* (2006.01)
*C08F 20/26* (2006.01)
*C08F 20/28* (2006.01)
*C08F 20/30* (2006.01)
*C08F 22/10* (2006.01)
*C08F 28/02* (2006.01)
*C08F 28/04* (2006.01)
*C08F 120/12* (2006.01)
*C08F 120/26* (2006.01)
*C08F 120/28* (2006.01)
*C08F 120/30* (2006.01)
*C08F 120/38* (2006.01)
(Continued)

(52) U.S. Cl.
CPC .............. *A61K 6/083* (2013.01); *A61K 6/0005* (2013.01); *A61K 6/09* (2013.01); *C08F 20/12* (2013.01); *C08F 20/26* (2013.01); *C08F 20/28* (2013.01); *C08F 20/30* (2013.01); *C08F 20/38* (2013.01); *C08F 22/105* (2013.01); *C08F 28/02* (2013.01); *C08F 28/04* (2013.01); *C08F 120/12* (2013.01); *C08F 120/26* (2013.01); *C08F 120/28* (2013.01); *C08F 120/30* (2013.01); *C08F 120/38* (2013.01); *C08F 122/105* (2013.01); *C08F 128/02* (2013.01); *C08F 128/04* (2013.01); *C08F 220/36* (2013.01); *C08F 220/38* (2013.01); *C08F 222/10* (2013.01); *C08F 228/02* (2013.01); *C08F 228/04* (2013.01); *C08L 33/08* (2013.01); *C08L 33/10* (2013.01); *C08L 35/02* (2013.01); *C08L 37/00* (2013.01); *C08L 39/04* (2013.01); *C08L 101/005* (2013.01); *C08F 2220/365* (2013.01); *C08F 2220/387* (2013.01); *C08F 2222/1013* (2013.01); *C08F 2222/1026* (2013.01)

(58) Field of Classification Search
USPC .................................................. 523/115, 116
IPC ............ A61K 6/0005,6/09, 6/083; C08L 33/08, C08L 33/10, 35/02, 37/00, 39/04, 101/005; C08F 20/12, 20/38, 20/26, 20/28, 20/30, C08F 28/02, 28/04, 22/105, 120/12, 120/26, C08F 120/28, 120/30, 120/38, 122/105, 128/02, C08F 128/04, 220/36, 220/38, 2220/365
See application file for complete search history.

(56) References Cited

U.S. PATENT DOCUMENTS 4,407,984 A * 10/1983 Ratcliffe et al. ................ 522/14
4,503,169 A 3/1985 Randklev
(Continued)

FOREIGN PATENT DOCUMENTS

EP 0319829 6/1989
EP 2008636 12/2008
(Continued)

OTHER PUBLICATIONS

International Search Report PCT/US2011/027523 Nov. 23, 2011, 6 pages.
(Continued)

*Primary Examiner* — Rabon Sergent
(74) *Attorney, Agent, or Firm* — Carolyn A. Fischer

(57) ABSTRACT

Polymerizable isocyanurate monomers and dental compositions are described. A hardenable dental composition is described comprising at least one isocyanurate monomer that is a stable liquid at about 25° C. The isocyanurate monomer comprises at least one divalent linking group bonded to a nitrogen atom of a trivalent isocyanuric acid ring, wherein the divalent linking group comprises a moiety selected from ester, thioester, ether, or thioether, and combinations of such moieties and a terminal ethylenically unsaturated polymerizable group.

23 Claims, No Drawings

(51) Int. Cl.
  *C08F 122/10* (2006.01)
  *C08F 128/02* (2006.01)
  *C08F 128/04* (2006.01)
  *C08F 220/36* (2006.01)
  *C08F 228/02* (2006.01)
  *C08F 228/04* (2006.01)
  *A61K 6/00* (2006.01)
  *A61K 6/09* (2006.01)
  *C08F 220/38* (2006.01)
  *C08F 222/10* (2006.01)

(56) References Cited

U.S. PATENT DOCUMENTS

| | | |
|---|---|---|
| 4,648,843 A | 3/1987 | Mitra |
| 4,762,863 A | 8/1988 | Sasaki |
| 5,130,347 A | 7/1992 | Mitra |
| 5,154,762 A | 10/1992 | Mitra |
| 5,302,630 A | 4/1994 | Mukai |
| 5,501,727 A | 3/1996 | Wang |
| 5,545,676 A | 8/1996 | Palazzotto |
| 5,962,550 A | 10/1999 | Akahane |
| 6,126,922 A | 10/2000 | Rozzi |
| 6,284,898 B1 | 9/2001 | Moszner |
| 6,387,981 B1 | 5/2002 | Zhang |
| 6,572,693 B1 | 6/2003 | Wu |
| 6,617,413 B1 | 9/2003 | Bruchmann |
| 6,670,436 B2 | 12/2003 | Burgath |
| 6,730,156 B1 | 5/2004 | Windisch |
| 6,794,520 B1 | 9/2004 | Moszner |
| 7,090,721 B2 | 8/2006 | Craig |
| 7,090,722 B2 | 8/2006 | Budd |
| 7,156,911 B2 | 1/2007 | Kangas |
| 7,241,437 B2 | 7/2007 | Davidson |
| 7,374,863 B2 | 5/2008 | Sugasaki |
| 7,649,029 B2 | 1/2010 | Kolb |
| 7,674,850 B2 | 3/2010 | Karim |
| 7,794,917 B2 | 9/2010 | Mori |
| 2003/0215750 A1 | 11/2003 | Inno |
| 2006/0216646 A1 | 9/2006 | Goto |
| 2007/0231745 A1 | 10/2007 | Oohashi |
| 2008/0194722 A1 | 8/2008 | Abuelyaman |
| 2009/0032989 A1 | 2/2009 | Karim |
| 2009/0111904 A1* | 4/2009 | Odaka et al. ............ 522/96 |
| 2010/0087611 A1 | 4/2010 | Urakawa |
| 2010/0160557 A1 | 6/2010 | Murofushi |

FOREIGN PATENT DOCUMENTS

| | | |
|---|---|---|
| EP | 2272486 | 1/2011 |
| JP | 60-123478 | 7/1985 |
| JP | 2001-39956 | 2/2001 |
| JP | 2009-74027 | 4/2009 |
| WO | WO 01/30305 | 5/2001 |
| WO | WO 01/30307 | 5/2001 |
| WO | WO 03/063804 | 8/2003 |
| WO | WO 2006/122081 | 11/2006 |
| WO | WO 2008/082881 | 7/2008 |
| WO | WO 2012/112321 | 8/2012 |

OTHER PUBLICATIONS

Surface & Colloid Science, vol. 6, Matijevic, E., Wiley Interscience, 1973.

Watts et al, "Determination of Polymerization Shrinkage Kinetics in Visible Light Cured Materials: Methods of Development", Dental Materials, Oct. 1991, pp. 281-286.

Mahmoodian et al., "Synthesis of organic-inorganic hybrid compounds based on Bis-GMA and its sol-gel behavior analysis using Taguchi method", Dental Materials 24 (2008) 514-521.

* cited by examiner

POLYMERIZABLE ISOCYANURATE MONOMERS AND DENTAL COMPOSITIONS

CROSS REFERENCE TO RELATED APPLICATIONS

This application is a national stage filing under 35 U.S.C. 371 of PCT/US2011/027523, filed Mar. 8, 2011, which claims priority to U.S. Provisional Application No. 61/319,534, filed Mar. 31, 2010, the disclosure of which is incorporated by reference in its entirety herein.

BACKGROUND

Various (meth)acrylate monomers have been employed in hardenable dental compositions.

U.S. Pat. No. 4,648,843 describes polymerizable carbamoyl isocyanurates in filled or unfilled dental materials such as restorative, prosthesis and sealant.

U.S. Pat. No. 5,302,630 describes a dental adhesive composition comprising, as the main components, (a) a polymer powder obtained by radical copolymerization of at least one (meth)acrylate unsaturated monomer containing no carboxyl or anhydride group in its molecule, with a silane compound having a polymerizable unsaturated group, (b) at least one radical polymerizable unsaturated monomer, and (c) a radical polymerization initiator. Column 2 describes an isocyanuric acid skeletal hexa-functional urethane (meth)acrylate as one type of a tri- or higher functional (meth)acrylate monomer containing no carboxyl or anhydride group.

U.S. Pat. No. 6,617,413 describes compounds having isocyanate groups with or without blocking, allophanate groups and free-radically polymerizable C—C double bonds, the C—C double bonds being in activated form by virtue of a carbonyl group attached directly to them or by virtue of an oxygen atom in ether function (activated double bonds), derived from polyisocyanates and alcohols A which in addition to the alcohol group also carry an activated double bond (compounds I). Column 5 depicts iso-cyanurate compounds. Also described is the use of such compound in radiation-curable dental compositions.

EP 2 008 636 relates to a dental composition comprising a) a hardenable compound (A1), b) a filler (B1), c) an initiator (C1) being able to initiate curing of compound (A1), compound (A1) having the structure A-(-S1-U-S2-MA)n, with A being a connector element, S1 being a spacer group comprised of units connected with each other and comprising at least 4 units, S2 being a spacer group comprised of units connected with each other and comprising at least 4 units, U being an urethane, an amide or an urea group connecting spacer groups S1 and S2, MA being an acrylate or methacrylate group and n being 3 to 6. The invention also relates to a process of producing this dental composition and using the dental composition e.g. as a temporary and/or long term crown and bridge material.

US2009/0032989 describes compositions, particularly for forming dental products, having a hardenable self-supporting structure with sufficient malleability to be subsequently customized into a second shape and then hardened, and methods. Paragraph 0026 states that, "In yet another preferred embodiment, a composition of the present invention includes a resin system comprising a crystalline compound of the formula:

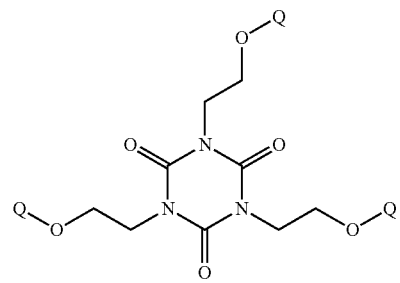

wherein each Q independently comprises polyester segments, polyamide segments, polyurethane segments, polyether segments, or combinations thereof; a filler system; and an initiator system; wherein the composition is in the form of a hardenable self-supporting structure having a first shape and sufficient malleability to be formed into a second shape."

Paragraphs 0135 and 0136 describe polymeric materials derived from the reaction of 1,3,5-tris(2-hydroxyethyl)cyanuric acid and ε-caprolactone. The resulting products were isolated as a solid or as a liquid that solidified.

SUMMARY

In one embodiment, a hardenable dental composition is described comprising at least one isocyanurate monomer that is a stable liquid at about 25° C., the monomer comprising at least one divalent linking group bonded to a nitrogen atom of a trivalent isocyanuric acid ring; wherein the divalent linking group comprises a moiety selected from ester, thioester, ether, or thioether, and combinations of such moieties and a terminal ethylenically unsaturated polymerizable group. In some embodiments, the divalent linking group comprises an aliphatic or aromatic diester linkage.

In a favored embodiment, the hardenable dental composition further comprises at least one (e.g. inorganic nanoparticle) filler. Such composition is suitable for use for dental adhesives, cements, and primers; dental filling materials; as well as dental articles such as crowns and bridges.

Also described are methods of treating a tooth surface using the hardenable dental compositions described herein.

In another embodiment, mono-, di-, and tri-(meth)acrylate isocyanurate monomers are described having the general formula

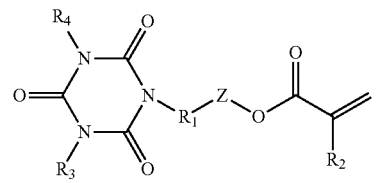

wherein $R_1$ is alkylene, arylene, or alkarylene, optionally including a heteroatom (e.g. oxygen, nitrogen, or sulfur); $R_2$ is hydrogen or methyl; Z is alkylene, arylene, or alkarylene linking group comprising at least one moiety selected from ester, thioester, ether, or thioether, and combinations of such moieties; and $R_3$ and $R_4$ are independently hydrogen, alkyl, aryl, or alkaryl, optionally including a heteroatom, or

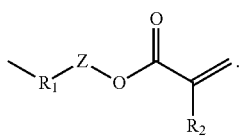

In one embodiment, the monomer has the general structure

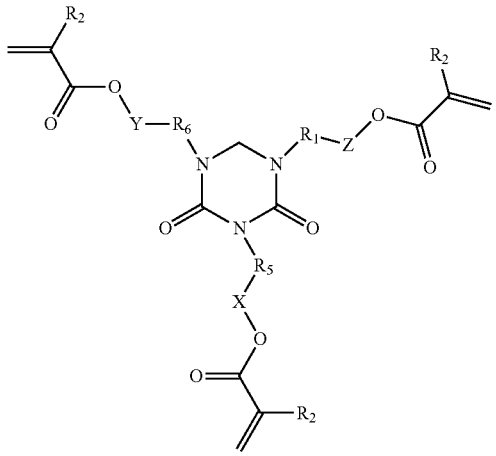

wherein
$R_1$, $R_5$, and $R_6$ are independently alkylene, arylene, or alkarylene, optionally including a heteroatom (e.g. oxygen, nitrogen, or sulfur); $R_2$ is hydrogen or methyl; X, Y, and Z are independently alkylene, arylene, or alkarylene linking group comprising at least one moiety selected from ester, thioester, ether, or thioether, and combinations of such moieties; and $R_2$ is hydrogen or methyl.

In some embodiments, $R_1$, $R_5$, and $R_6$ comprise at least one hydroxyl moiety.

DETAILED DESCRIPTION

As used herein, "dental composition" refers to an unfilled material (i.e. total dental composition except for filler) or filled material (e.g., a dental cement or restoration) capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth and subsequently adhered in placed in the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns and bridges. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

As used herein, "dental article" refers to an article that can be adhered (e.g., bonded) to a tooth structure. Dental articles include, for example, crowns, bridges, veneers, inlays, onlays, fillings, orthodontic appliances and devices.

As used herein, "orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

As used herein, an "oral surface" refers to a soft or hard surface in the oral environment. Hard surfaces typically include tooth structure including, for example, natural and artificial tooth surfaces, bone, and the like.

As used herein, "hardenable" is descriptive of a material or composition that can be cured (e.g., polymerized or crosslinked) by heating to induce polymerization and/or crosslinking; irradiating with actinic irradiation to induce polymerization and/or crosslinking; and/or by mixing one or more components to induce polymerization and/or crosslinking "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked).

As used herein, "hardener" refers to something that initiates hardening of a resin. A hardener may include, for example, a polymerization initiator system, a photoinitiator system, a thermal initiator and/or a redox initiator system.

As used herein, the term "(meth)acrylate" is a shorthand reference to acrylate, methacrylate, or combinations thereof; "(meth)acrylic" is a shorthand reference to acrylic, methacrylic, or combinations thereof; and "(meth)acryl" is a shorthand reference to acryl, methacryl, or combinations thereof.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The dental compositions described herein comprise at least one isocyanurate monomer. Such monomers comprise a trivalent isocyanuric acid ring as an isocyanurate core structure and at least one ethylenically unsaturated (e.g. free radically) polymerizable groups bonded to at least one of nitrogen atoms of the isocyanurate core structure via a (e.g. divalent) linking group. The linking group is the entire chain of atoms between the nitrogen atom of the isocyanurate core structure and the terminal ethylenically unsaturated (e.g. free radically polymerizable e.g. ((meth)acrylate) group).

The trivalent isocyanurate core structure generally has the formula:

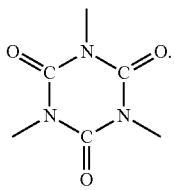

The divalent linking group comprises an oxygen or sulfur atom. Such oxygen or sulfur atom forms an ester, thioester, ether, or thioether linkage. Such linkages can be beneficial over isocyanurate monomers comprising urethane linkages. For example, it has been found that the dental compositions described herein can provide improved properties such as reduced shrinkage, and/or increased mechanical properties, e.g., diametal tensile strength (DTS). Thus, in some embodiments, the divalent linking group is free of urethane linkages.

In some embodiments, the divalent linking group comprises an aliphatic or aromatic diester linkage. The linking group(s) is typically sufficiently low in molecular weight such that the monomer is a stable liquid at 25° C. However, the linking group(s) is typically higher in molecular weight than the oxygen atom of for example 2,2-bis[4-(2-hydroxy-3-methacryloyloxypropoxy)phenyl]propane ("BisGMA"), a common monomer utilized in dental compositions, that links the (meth)acrylate group to the aromatic ring. The molecular weight of the linking group(s) of the isocyanurate monomers described is typically at least 50 g/mole or 100 g/mole. In some embodiments, the molecular weight of the linking group is at least 150 g/mole. The molecular weight of the linking group is typically no greater than about 500 g/mole. In some embodiments, the molecular weight of the linking group is no greater than 400 g/mole or 300 g/mole.

The (i.e. calculated) molecular weight of the monomer of this invention is typically no greater than 2000 g/mole. In some embodiments, the molecular weight of the isocyanurate monomer is no greater than about 1500 g/mole or 1000 g/mole. The molecular weight of the monomer is typically at least 500 g/mole for the mono(meth)acrylate isocyanurate monomer having no further substituents on the isocyanurate core structure.

Increasing the molecular weight without forming a solid at 25° C. can be achieved by various synthetic approaches. In some embodiments, the linking group has one or more pendant substituents. For example, the linking group(s) may comprise one or more hydroxyl group substituents such an in the case of linking groups comprising alkoxy segments. In other embodiments, the linking group is branched, and/or comprises at least one (i.e. aliphatic) cyclic moiety, and/or comprises at least one aromatic moiety.

The inclusion of sulfur atoms and/or the present of one or more aromatic moieties can result in isocyanurate monomers having a refractive index of at least 1.50. In some embodiments, the refractive index is at least 1.51, 1.52, 1.53, or greater.

The divalent linking group(s) comprises a terminal ethylenically unsaturated terminal polymerizable group. In favored embodiment, such ethylenically unsaturated group is a free radically polymerizable group. The ethylenically unsaturated terminal polymerizable group(s) including (meth) acryl such as (meth)acrylamide ($H_2C=CHCON—$ and $H_2C=CH(CH_3)CON—$) and (meth)acrylate ($CH_2CHCOO—$ and $CH_2C(CH_3)COO—$). Other ethylenically unsaturated polymerizable groups include vinyl ($H_2C=C—$) including vinyl ethers ($H_2C=CHOCH—$). The ethylenically unsaturated terminal polymerizable group(s) is preferably a (meth)acrylate group, particularly for compositions that are hardened by exposure to actinic (e.g. UV) radiation. Further, methacrylate functionality is typically preferred over the acrylate functionality in curable dental compositions.

The isocyanurate monomer typically has the general structure

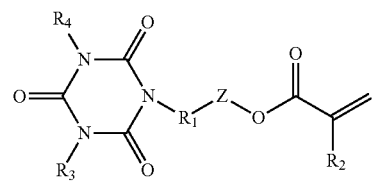

wherein $R_1$ is a straight chain, branched or cyclic alkylene, arylene, or alkarylene, optionally including a heteroatom (e.g. oxygen, nitrogen, or sulfur); $R_2$ is hydrogen or methyl; Z is alkylene, arylene, or alkarylene linking group comprising at least one moiety selected from ester, thioester, ether, or thioether, and combinations of such moieties; and $R_3$ and $R_4$ are independently hydrogen, alkyl, aryl, or alkaryl, optionally including a heteroatom, or

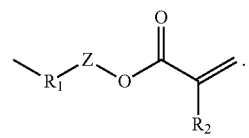

$R_1$ is typically a straight chain, branched or cyclic alkylene, optionally including a heteroatom, having no greater than 12 carbons atoms. In some favored embodiments, $R_1$ has no greater than 8, 6, or 4 carbon atoms. In some favored embodiments, $R_1$ comprises at least one hydroxyl moiety.

In some embodiments, Z comprises an aliphatic or aromatic diester linkage.

In some embodiment, Z further comprises one or more ether moieties. Hence, the linking group may comprise a combination of ester or diester moieties and one or more ether moieties.

$R_1$ is generally derived from the starting (e.g. hydroxyl terminated) isocyanurate precursor. Various isocyanurate precursor materials are commercially available from TCI America, Portland, Oreg. The structures of exemplary isocyanurate precursor materials are depicted as follows:

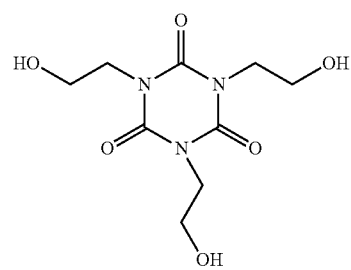

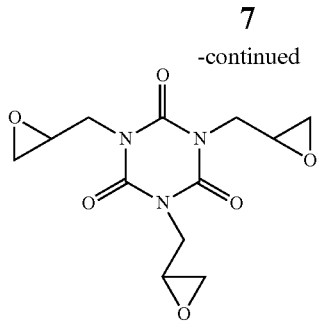

The isocyanurate (meth)acrylate monomers disclosed herein having a linking groups comprising an oxygen atom of an ester moiety were generally prepared by reaction of hydroxy or epoxy terminated isocyanurates with (meth)acrylated carboxylic acids such as mono-(2-methacryloxyethyl) phthalic acid and mono-(2-methacryloxytheyl)succinic acid.

Suitable (meth)acrylated or (meth)acrylamidated carboxylic acids include for example mono-(2-methacryloxyethyl) phthalic acid(s), mono-(2-methacryloxytheyl)succinic acid, mono-(2-methacryloxyethyl)maleic acid, methacrylamido derivatives of naturally occurring amino acids such as mehtacrylamidoglycine, mehtacrylamidoleucine, mehtacrylamidoalanine etc.

In some embodiments, a single(meth)acrylated carboxylic acid is reacted with a single hydroxyl terminated isocyanurate (e.g. tris-(2-hydroxylethyl)isocyanurate). When a sufficient molar ratio of (meth)acrylate carboxylic acid is utilized such that all the hydroxyl groups of the ring are reacted, such synthesis can produce a single reaction product wherein each of the free radically terminated groups, bonded to the nitrogen atoms of the trivalent isocyanuric acid ring, are the same.

However, when a single epoxy terminated isocyanurate is reacted with a single carboxylic acid, the reaction product generally comprises more than one isomer in the reaction product.

When two different hydroxy or epoxy terminated isocyanurates and/or two different (meth)acrylated carboxylic acids are utilized, a statistical mixture of reaction products are obtained based on the relative amounts of reactants. For example, when a mixture of a (meth)acrylated aromatic carboxylic acid and a (meth)acrylate aliphatic carboxylic acid are utilized, some of the free radically terminated divalent linking groups bonded to the nitrogen atom of the trivalent isocyanuric acid ring comprise an aromatic group, whereas others do not. Further, when a combination (e.g. 1 equivalent) of a hydroxyl terminated carboxylic acid and (e.g. 2 equivalents) of a monocarboxylic acid (such as octanoic acid) is reacted with a single hydroxyl terminated isocyanurate (e.g. tris-(2-hydroxylethyl)isocyanurate), a mono(meth)acrylate isocyanurate can be prepared as further described in the forthcoming examples.

Alternatively, isocyanurate (meth)acrylate monomers having ether group containing linking groups can be synthesized. For example, in one illustrative synthesis, phthalic acid anhydride can be reacted with a mono-methacrylated di, tri, tetra or polyethylenegylcol in the presence of a catalytic amount of 4-(dimethylamino)pyridine (DMAP) and butylated hydroxytoluene inhibitor (BHT) at 95° C. for a 3-6 hours to form a mono-methaycrylated polyethyleneglycol phthalic acid mono-ester. The obtained methacrylated acid can be reacted, in acetone, with tris-(2-hydroxyethyl)isocyanurate using dicyclohexyl carbodiimide (DCC) at 0-5° C. then at room temperature. Such reaction scheme is depicted as follows:

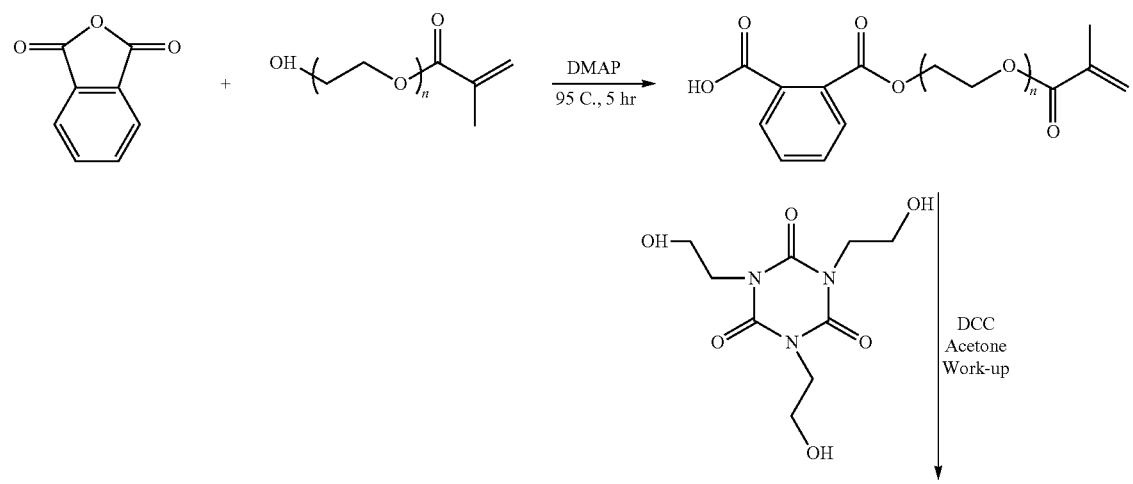

-continued

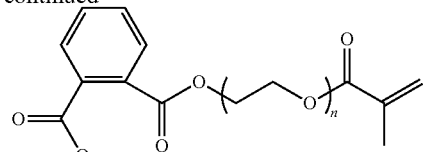
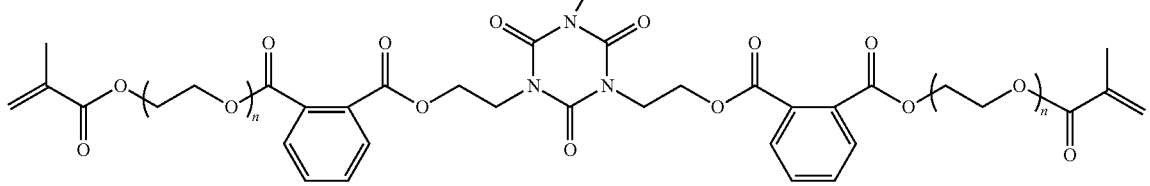

In another illustrative synthesis, tris(2-hydroxyethyl)isocyanurate can be reacted with ethylene oxide to form a polyethylene glycol terminated with a hydroxyl group. The OH termini can be esterified with meth(acrylic) acid to provide a product where the linking group is a polyether. Such reaction scheme is depicted as follows:

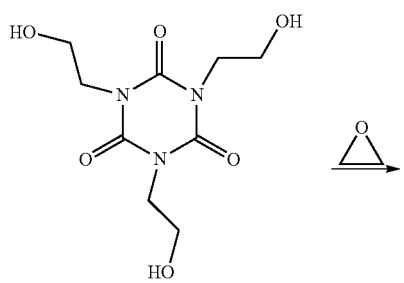

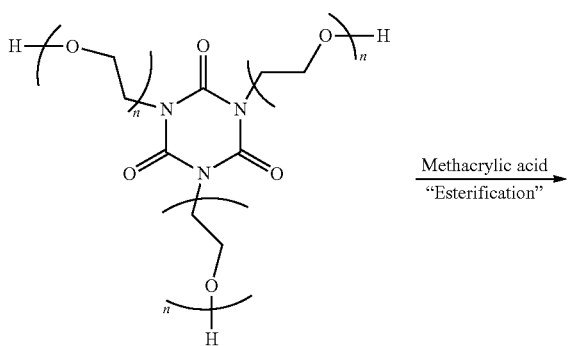

-continued

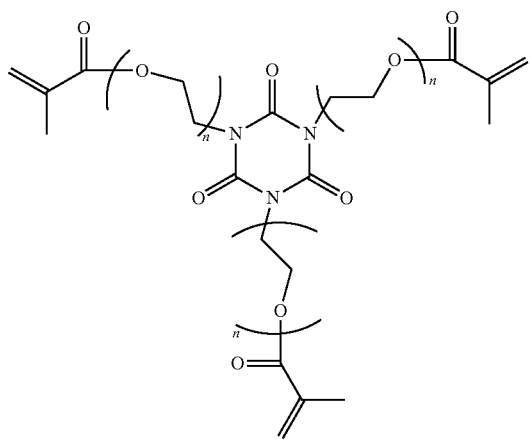

In some embodiments, a by-product is formed that may be a solid at about 25° C. (i.e. +/−2° C.). Such by-product is typically removed from the liquid monomer. Hence, the liquid monomer is substantially free of such solid fractions. However, it is contemplated that the liquid monomer may further comprise (e.g. non-crystalline) solid reaction by-products that are soluble in the liquid monomer.

In some embodiments, the (e.g. mono(meth)acrylate) liquid isocyanurate monomer is relatively low in viscosity at about 25° C. and thus can function as a reactive diluent. In other embodiments, the (e.g. multi(meth)acrylate) liquid isocyanurate monomer is a (e.g. highly) viscous liquid at about 25° C., yet is flowable.

In favored embodiments, the isocyanurate monomers described herein are stable liquids at about 25° C. meaning that the monomer do not substantially polymerize, crystallize, or otherwise solidify when stored at room temperature (about 25° C.) for a typical shelf life of at least 30, 60, or 90 days. The viscosity of the isocyanurate typically does not change (e.g. increase) by more than 10% of the initial viscosity.

In some embodiments, the isocyanurate monomer is a mono(meth)acrylate isocyanurate monomer. One illustrative monomer is:

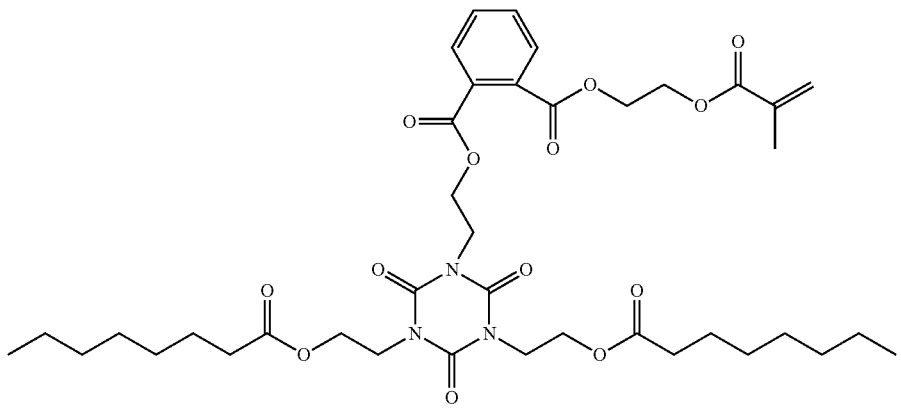 [SMILES: C=C(C)C(=O)OCCOC(=O)c1ccccc1C(=O)OCCn1c(=O)n(CCOC(=O)CCCCCCC)c(=O)n(CCOC(=O)CCCCCCC)c1=O]

The mono(meth)acrylate isocyanurate monomers are preferably sufficiently low in viscosity such that the monomers are suitable for use as a reactive diluent in combination with at least one multi(meth)acrylate monomer. Such multi(meth)acrylate monomer may be a multi(meth)acrylate isocyanurate monomer, as described herein, or a different (i.e. non-isocyanurate) monomer such as BisGMA. In one embodiment, the isocyanurate monomers is synthesized such that the reaction product contains a portion of mono(meth)acrylate isocyanurate monomer in combination with multi(meth)acrylate isocyanuratemonomer.

The other embodiments, the isocyanurate monomer is a multi(meth)acrylate such as a di(meth)acrylate isocyanurate monomer or a tri(meth)acrylate isocyanurate monomer. The di(meth)acrylate monomer has the general structure:

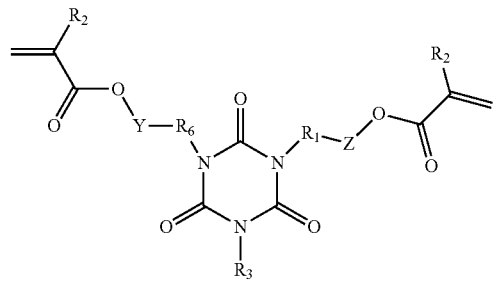

wherein $R_1$, $R_2$, $R_3$ and Z are as previously described; $R_6$ is a straight chain, branched, or cyclic alkylene, arylene, or alkarylene, optionally including a heteroatom (e.g. oxygen, nitrogen, or sulfur); and Y is alkylene, arylene, or alkarylene linking group comprising at least one moiety selected from ester, thioester, ether, or thioether, and combinations of such moieties.

One illustrative di(meth)acrylate isocyanurate monomers includes:

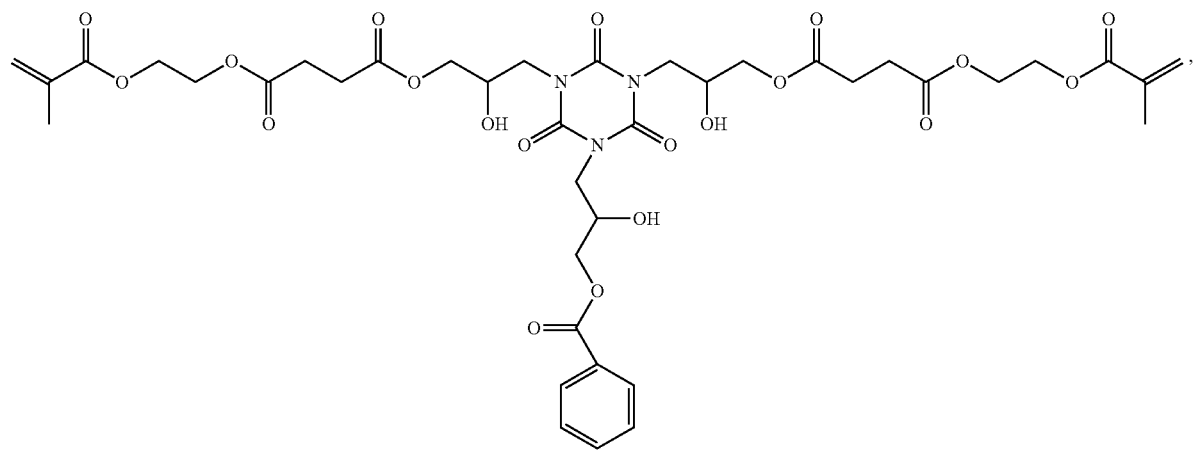

-continued

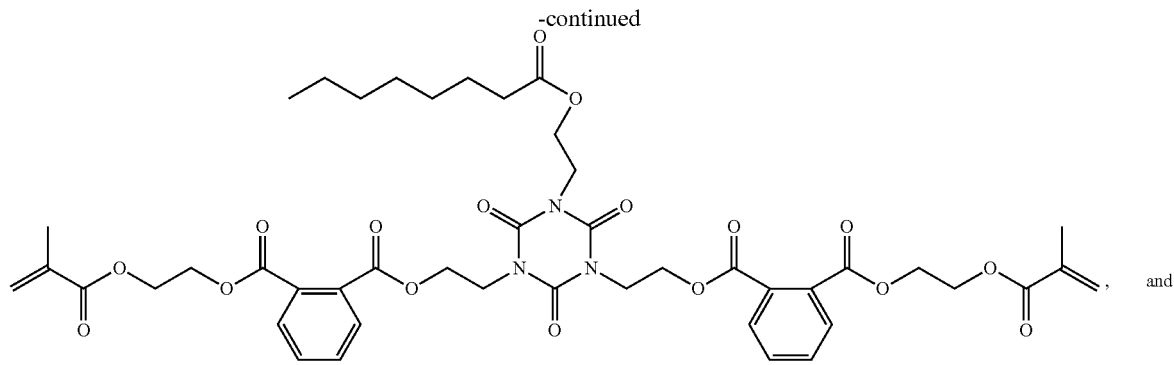

, and

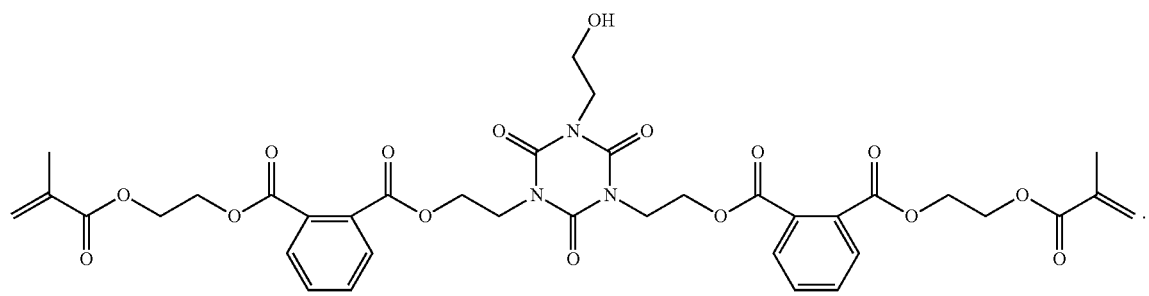

.

In some favored embodiments, the tri(meth)acrylate monomer has the general structure:

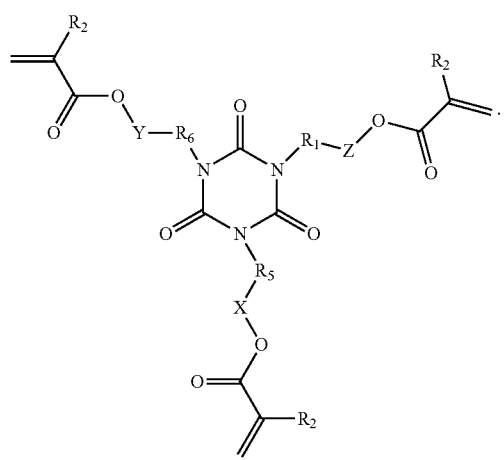

wherein $R_1$, $R_5$, and $R_6$ are independently a straight chain, branched, or cyclic alkylene, arylene, or alkarylene, optionally including a heteroatom (e.g. oxygen, nitrogen, or sulfur); $R_2$ is hydrogen or methyl; X, Y, and Z are independently alkylene, arylene, or alkarylene linking group comprising at least one moiety selected from ester, thioester, ether, thioether, or combinations of such moieties; and $R_2$ is hydrogen or methyl.

In some embodiments, $R_1$, $R_5$, and $R_6$ comprise at least one hydroxyl moiety.

Illustrative tri(meth)acrylate isocyanurate monomers include for example:

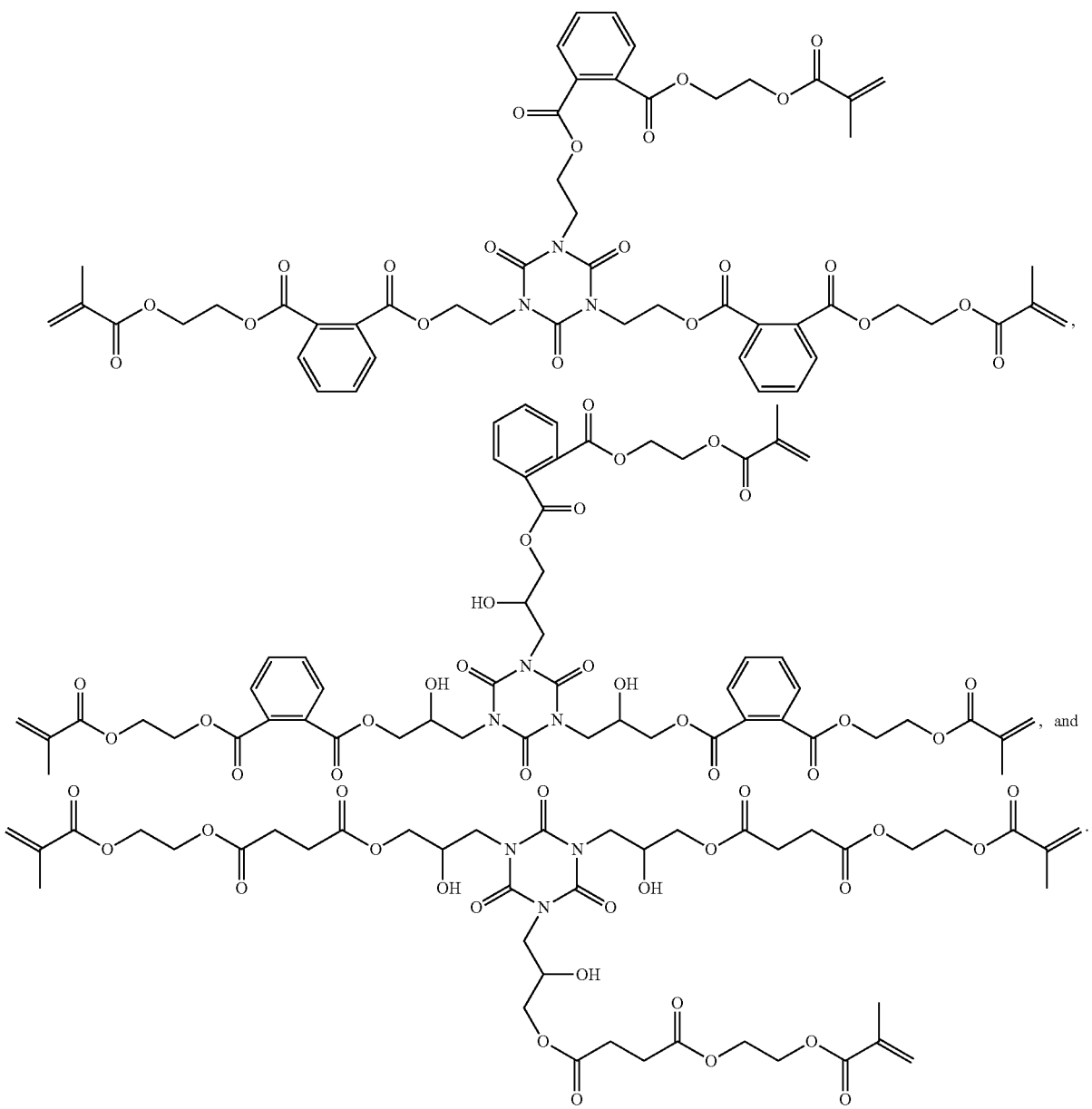

The multi(meth)acrylate isocyanurate monomers are typically viscous liquids at 25° C. The isocyanurate multi(meth)acrylate liquid monomer may be present in the curable dental composition at a weight percentage of 1 to 99.95%.

The isocyanurate monomers described herein, and in particular such tri-(meth)acrylate monomers, advantageously have been found to have a low volume shrinkage. Preferred isocyanurate (meth)acrylate monomers and (e.g. filled) dental compositions (useful for restorations such as fillings and crowns) described herein typically exhibit a Watts Shrinkage of less than about 2%. In some embodiments, the Watts Shrinkage is not greater than 1.95%, or no greater than 1.90%, or no greater than 1.85%, or no greater than 1.80%. In favored embodiments, the Watts Shrinkage is no greater than 1.75%, or no greater than 1.70%, or no greater than 1.65%, or no greater than 1.60%, or no greater than 1.55%, or no greater than 1.50%, or no greater than 1.45%, or no greater than 1.40%.

In some embodiments, a polymerizable (e.g. multi(meth)acrylate) isocyanurate liquid monomer, as described herein, is employed as the primary or sole polymerizable organic component, typically in combination with a polymerization initiator, such as a photoinitiator. In other embodiments, the dental composition comprises a mixture of polymerizable isocyanurate liquid monomer(s) such as a mono(meth)acrylate isocyanurate monomer and a multi(meth)acrylate isocyanurate monomer. In such embodiments, the total concentration of isocyanurate (meth)acrylates in the (unfilled) curable dental composition is typically about 95 wt-%, 96 wt-%, 97 wt-%, or about 98 wt-%.

In other embodiments, the polymerizable isocyanurate liquid monomer(s) are employed in combination with other conventional (e.g. (meth)acrylate) ethylenically unsaturated monomer(s), oligomer(s), or polymer(s). By "other" is it meant an ethylenically unsaturated monomer that is not an isocyanurate multi(meth)acrylate In one favored embodiments, multi(meth)acrylate isocyanurate monomers are combined with other (meth)acrylate monomers having a low volume shrinkage (i.e. a monomer that exhibits a Watts Shrinkage of about 2% and preferable less than 2% as previously described.)

Preferred low volume shrinkage monomers include polymerizable compounds having at least one cyclic allylic sulfide moiety such as described in US2008/0194722, methylene dithiepane silanes as described in U.S. Pat. No. 6,794,520, oxetane silanes such as described in U.S. Pat. No. 6,284,898, and di-, tri, and/or tetra-(meth)acryloyl-containing materials such as described in WO2008/082881; each of which are incorporated herein by reference.

US2008/0194722 describes a polymerizable compound having at least one cyclic allylic sulfide moiety with at least one (meth)acryloyl moiety.

Such a polymerizable compound is referred to herein as a hybrid monomer or a hybrid compound. The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, SO$_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have two or more cyclic allylic sulfide moieties. The (meth)acryloyl moiety is preferably a (meth)acryloyloxy (i.e. a (meth)acrylate moiety) or a (meth)acryloylamino (i.e., a (meth)acrylamide moiety).

In one embodiment, the other low shrinkage monomer includes those represented by the formulae:

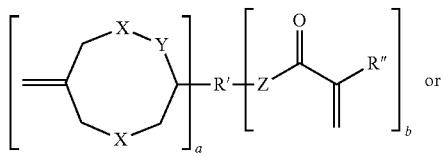

Formula Ia

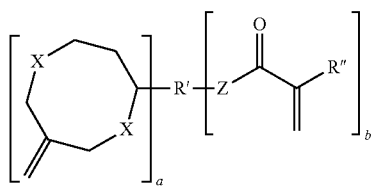

Formula Ib

In the above formulae, each X can be independently selected from S, O, N, C (e.g., CH$_2$ or CRR, where each R is independently a H or an organic group), SO, SO$_2$, N-alkyl, N-acyl, NH, N-aryl, carboxyl or carbonyl group, provided that at least one X is S or a group comprising S. Preferably, each X is S.

Y is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with Y thus being either absent or methylene, respectively. In some embodiments, Y is either absent or is a C1 to C3 alkylene, optionally including a heteroatom, carbonyl, acyl, or combinations thereof.

Z is O, NH, N-alkyl (straight chain or branched), or N-aryl (phenyl or substituted phenyl).

The R' group represents a linker selected from alkylene (typically having more than one carbon atom, i.e. excluding methylene), alkylene optionally including a heteroatom (e.g., O, N, S, S—S, SO, SO2), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, alkylthio, carbonyl, acyl, acyloxy, amido, urethane group, urea group, a cyclic allylic sulfide moiety, or combinations thereof.

R" is selected from H, and CH$_3$, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, alkylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

A typical low shrinkage monomer can comprise an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

Representative polymerizable compounds having at least one cyclic allylic sulfide moiety with at least one (meth)acryloyl moiety include the following

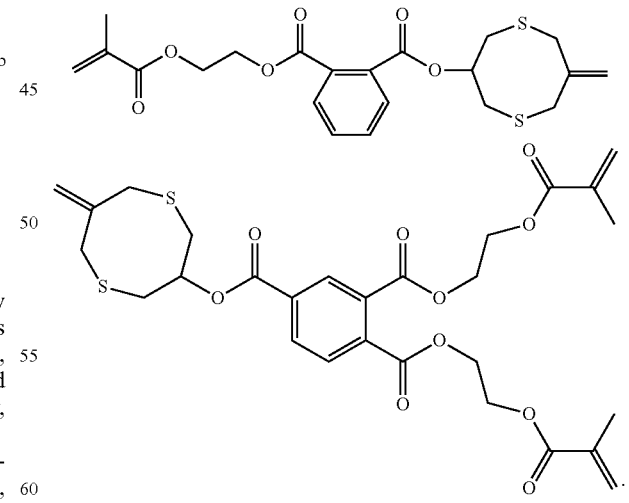

Other suitable monomers are described in US2008/0194722.

In another embodiment, the other low shrinkage monomer includes at least one di-, tri-, and/or tetra(meth)acryloyl-containing materials having the general formula:

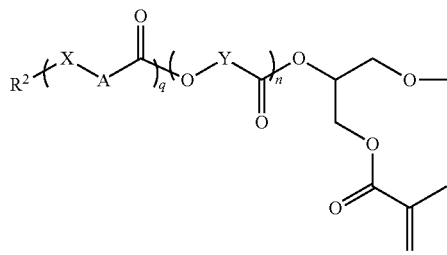 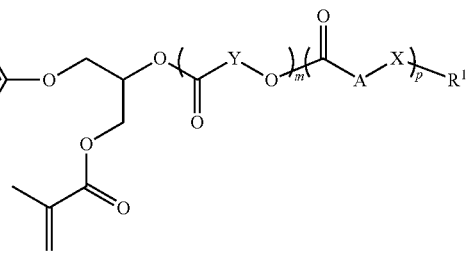

wherein: each X independently represents an oxygen atom (O) or a nitrogen atom (N); Y and A each independently represent an organic group, with the proviso that Y does not represent —NHCH$_2$CH$_2$— if (i) p=0 and R$^1$ represents —C(O)C(CH$_3$)=CH$_2$, and/or (ii) q=0 and R$^2$ represents —C(O)C(CH$_3$)=CH$_2$; m=1 to 5; n=0 to 5; p and q are independently 0 or 1; and R$^1$ and R$^2$ each independently represent H, —C(O)CH=CH$_2$, or —C(O)C(CH$_3$)=CH$_2$.

In some embodiments, the (i.e. unfilled) polymerizable dental composition comprises at least 40 wt-%, 45 wt-%, or 50 wt-% of one or more isocyanurate multi(meth)acrylate monomers as described herein in combination with 10 wt-%, 15 wt-%, 20 wt-%, 25 wt-%, or 30 wt-% of a low volume shrinkage monomer having at least one cyclic allylic sulfide moiety with at least one (meth)acryloyl moiety (such as the species just described). Such a blend can result in a synergistic combination of low volume shrinkage in combination with high diametral tensile strength.

In some embodiment, the polymerizable isocyanurate liquid monomer can be used in place of conventional hardenable (meth)acrylate monomers, such as ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylglycol dimethacrylate (NPGDMA), and polyethyleneglycol dimethacrylate (PEGDMMA). In one embodiment, the polymerizable isocyanurate liquid monomer is used in place of (meth)acrylate monomers formed from bisphenol A and thus the dental composition is free of (meth)acrylate monomers formed from bisphenol A.

In other embodiments, the polymerizable isocyanurate liquid monomer can be used in combination with one or more of such conventional hardenable (meth)acrylate monomers. For example, the (e.g. filled) dental composition may comprise at least 5 wt-% or 10 wt-% of urethane dimethacrylate (UDMA). The urethane dimethacrylate (UDMA) functions as a reactive diluent for the viscous (e.g. di- and tri-(meth) acrylate) isocyanurate monomers described herein.

The curable component of the curable dental composition can include a wide variety of other ethylenically unsaturated compounds (with or without acid functionality), epoxy-functional (meth)acrylate resins, vinyl ethers, and the like.

The (e.g., photopolymerizable) dental compositions may include free radically polymerizable monomers, oligomers, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri (meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth) acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are available from a wide variety of commercial sources, such as Sigma-Aldrich, St. Louis.

The dental compositions described herein may include one or more curable components in the form of ethylenically unsaturated compounds with acid functionality. Such components contain acidic groups and ethylenically unsaturated groups in a single molecule. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl)phosphate, bis((meth)acryloxypropyl)phosphate, bis((meth)acryloxy)propyloxy phosphate, (meth)acryloxyhexyl phosphate, bis((meth)acryloxyhexyl)phosphate, (meth)acryloxyoctyl phosphate, bis ((meth)acryloxyoctyl)phosphate, (meth)acryloxydecyl phosphate, bis((meth)acryloxydecyl)phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components. Also monomers, oligomers, and polymers of unsaturated carbonic acids such as (meth)acrylic acids, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler.

The curable dental compositions can include at least 1 wt-%, at least 3 wt-%, or at least 5 wt-% ethylenically unsaturated compounds with acid functionality, based on the total weight of the unfilled composition. The compositions can include at most 80 wt-%, at most 70 wt-%, or at most 60 wt-% ethylenically unsaturated compounds with acid functionality.

The curable dental compositions may include resin-modified glass ionmers cements such as those described in U.S. Pat. No. 5,130,347 (Mitra) U.S. Pat. No. 5,154,762 (Mitra) U.S. Pat. No. 5,962,550 (Akahane). Such compositions can be powder-liquid, paste-liquid or paste-paste systems. Alternatively, copolymer formulations such as those described in U.S. Pat. No. 6,126,922 (Rozzi) are included in the scope of the invention.

An initiator is typically added to the (e.g. multifunctional) polymerizable isocyanurate liquid monomer or to the mixture of polymerizable ingredients comprising at least one (e.g. multifunctional) polymerizable isocyanurate liquid monomer, as described herein. The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

In some embodiments, the (e.g. multifunctional) polymerizable isocyanurate liquid monomer or composition comprising such is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2, 4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays. For this embodiment, suitable photoinitiators include those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The dental compositions comprising the polymerizable isocyanurate liquid monomer may be chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

Curable dental compositions can also be cured with a thermally or heat activated free radical initiator. Typical thermal initiators include peroxides such as benzoyl peroxide and azo compounds such as azobisisobutyronitrile.

In some embodiments, such as when the dental composition is employed as a dental restorative (e.g. dental filling or crown) or an orthodontic adhesive, the dental composition typically comprises appreciable amounts of (e.g. nanoparticle) filler. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

In such dental compositions comprising appreciable amounts of filler, the one or more (e.g. multifunctional) polymerizable isocyanurate liquid monomers are typically present in an amount totaling at least 5 wt-%, 6 wt-%, 7 wt-%, 8 wt-%, 9 wt-%, or 10 wt-%, based on the total weight of the composition. The concentration of (e.g. multifunctional) polymerizable isocyanurate liquid monomers is generally no greater than about 60 wt-%. In some embodiments the total amount of (e.g. multifunctional) polymerizable isocyanurate liquid monomers is at most 40 wt-%, preferably at most 30 wt-%, and more preferably at most 25 wt-%.

The (e.g. filled) dental composite materials typically exhibit a diametral tensile strength (DTS) of at least about 70, 75, or 80 MPa and/or a Barcol Hardness of at least about 80 or 85. The depth of cure and staining resistance is about comparable to commercially available (e.g. filled) dental compositions suitable for restorations.

For embodiments wherein the (e.g. multifunctional) polymerizable isocyanurate liquid monomer is employed as an adhesive or cement, the amount of (e.g. multifunctional) polymerizable isocyanurate liquid monomer(s) can be considerably higher. For example, a (e.g. multifunctional) polymerizable ionic that is a liquid at 25° C., may be employed as the sole polymerizable component.

Dental compositions suitable for use as dental adhesives can also include filler in amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Non-acid-reactive inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. No. 7,156,911; and U.S. Pat. No. 7,649,029 (Kolb et al.).

Examples of suitable organic filler particles include filled or unfilled pulverized polycarbonates, polyepoxides, poly(meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO 1041.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin. Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formulas: $CH_2=C(CH_3)_m Si(OR)_n$ or $CH_2=C(CH_3)_m C=OOASi(OR)_n$; wherein m is 0 or 1, R is an alkyl group having 1 to 4 carbon atoms, A is a divalent organic linking group, and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependant upon several factors such as particle size, particle type, modifier molecular wt, and modifier type. In general it is preferred that approximately a monolayer of modifier is attached to the surface of the particle.

The surface modified nanoparticles can be substantially fully condensed. Fully condensed nanoparticles (with the exception of silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g. zirconia) nanoparticles have a high refractive index whereas amorphous nanoparticles typically have a lower refractive index.

In some embodiments, the dental compositions can have an initial color remarkably different than the cured dental structures. Color can be imparted to the composition through the use of a photobleachable or thermochromic dye. As used herein, "photobleachable" refers to loss of color upon exposure to actinic radiation. The composition can include at least 0.001 wt-% photobleachable or thermochromic dye, and typically at least 0.002 wt-% photobleachable or thermochromic dye, based on the total weight of the composition. The composition typically includes at most 1 wt-% photobleachable or thermochromic dye, and more typically at most 0.1 wt-% photobleachable or thermochromic dye, based on the total weight of the composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. The photobleachable dye is generally at least partially soluble in a hardenable resin.

Photobleachable dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change can be initiated by actinic radiation such as provided by a dental curing light which emits visible or near infrared (IR) light for a sufficient amount of time. The mechanism that initiates the color change in the compositions may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT,), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. Dental adhesives are also hardened by curing after applying the dental composition to the tooth. The method of treating an oral surface may comprise providing a dental article and adhering the dental article to an oral (e.g. tooth) surface. The dental article may comprise a cured composition comprising a polymerizable isocyanurate liquid monomer as described herein.

In other embodiments, the compositions can be hardened (e.g., polymerized) into dental articles prior to applying. For example, a dental article such as a crown may be pre-formed from the hardenable dental composition described herein. Dental composite (e.g. crowns) articles can be made from the curable composition described herein by casting the curable composition in contact with a mold and curing the composition. Alternatively, dental composite (e.g. crowns) article can be made by first curing the composition forming a mill blank and then mechanically milling the composition into the desired article.

Another method of treating a tooth surface comprises providing a dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in U.S. Pat. No. 7,674,850 (Karim et al.); incorporated herein by reference.

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

EXAMPLES

Test Methods

1. Watts Shrinkage

The Watts Shrinkage (Watts) Test Method measures shrinkage of a test sample in terms of volumetric change after curing. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. Results in terms of percent shrinkage were reported as the average of three replicates for each sample.

2. Diametral Tensile Strength (DTS) Test Method

Diametral tensile strength of a test sample was measured according to the following procedure. An uncured composite sample was injected into a 4-mm (inside diameter) glass tube; the tube was capped with silicone rubber plugs. The tube was compressed axially at approximately 2.88 kg/cm$^2$ pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany). The sample was cut with a diamond saw to form disks about 2 mm thick, which were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Results are reported in MPa as the average of multiple measurements.

3. Barcol Hardness

Barcol Hardness of a test sample was determined according to the following procedure. An uncured composite sample was cured in 2.5-mm thick TEFLON mold sandwiched between a sheet of polyester (PET) film and a glass slide for 30 seconds and cured with an ELIPAR Freelight 2 dental curing light (3M Company). After irradiation, the PET film was removed and the hardness of the sample at both the top and the bottom of the mold was measured using a Barber-Coleman Impressor (a hand-held portable hardness tester; Model GYZJ 934-1; Barber-Coleman Company, Industrial Instruments Division, Lovas Park, Ind.) equipped with an indenter. Top and bottom Barcol Hardness values were measured at 5 minutes after light exposure. Results were reported as the average of three measurements.

4. Depth of Cure

The depth of cure was determined by filling a 10 millimeter stainless steel mold cavity with the composite, covering the top and bottom of the mold with sheets of polyester film, pressing the sheets to provide a leveled composition surface, placing the filled mold on a white background surface, irradiating the dental composition for 20 seconds using a dental curing light (3M Dental Products Curing Light 2500 or 3M ESPE Elipar FreeLight2, 3M ESPE Dental Products), separating the polyester films from each side of the mold, gently removing (by scraping) materials from the bottom of the sample (i.e., the side that was not irradiated with the dental curing light), and measuring the thickness of the remaining material in the mold. The reported depths are the actual cured thickness in millimeters divided by 2.

5. Staining (Coffee)

Staining Disk Preparation

Samples (approximately 10 grams) of the dental compositions were pressed to a thickness of approximately 1.1 millimeters (between 2 pieces of silicone release paper), using a hydraulic press (available from Carver Inc., Wabash, Ind.) at approximately 60° C. Each pressed sample was then stored at room temperature for 5 days, after which a 14 mm diameter disc was cut and placed in a 1 mm thick by 15 mm diameter split mold, sandwiched between 2 pieces of 1 mil polyester film available from DuPont under the trade designation "Mylar". This was then placed between 2 steel plates, and pressed in the above hydraulic press at 37° C. for 2 minutes under 1000 psi (6.9×10$^6$ Pa). The polyester film sandwiched sample was then taken out of the hydraulic press, covered with a 1 mm thick, 50 mm×75 mm glass microscope slide (VWR Catalog #374-1407) over the polyester film, and light cured for 50 seconds by using VISILUX Model 2500 dental curing light. After that, the other side was also cured for 50 seconds through a glass microscope slide. With the polyester films still present, the dental composite disc was conditioned in a 37° C. oven for 15 minutes. This sample disc was then stored in 37° C. deionized water before staining test.

Coffee Solution

A 15% coffee solution was prepared by adding 15 g of Folgers Classic Roast Instant Coffee Crystals to 85 g of 80° C. de-ionized water, mixing well, and then letting it cool down to 37° C. or less. (coffee crystals commercially available from The Folger Coffee Company, Cincinnati, Ohio 45202).

Two discs were used from each formulation for the staining test. The CIELAB color of each disc was measured before the staining test as follows. A spectrophotometer obtained from HunterLab, Reston, Va. under the trade designation "UltraScan XE" in small area view mode with RSIN (reflectance specular included) was used to measure the L*, a*, and b* values. After the initial color measurements, the dental composite discs were placed in the indicated test solution for the specified duration of time. The stained discs were then rinsed with de-ionized water, and the color of the stained discs was measured again. The staining resistance is reported as $\Delta E^*$ as defined below:

$$\Delta E^* = [(L_0^* - L_1^*)^2 + (a_0^* - a_1^*)^2 + (b_0^* - b_1^*)^2]^{1/2}$$

wherein each 0 represents the initial values and each 1 represents the values after conditioning the hardened dental composition in the indicated test solution.

Refractive Index Measurement

Refractive Index was measured at Room Temperature on a Refractometer manufactured by Bausch & Lomb (Rochester, N.Y., USA), Cat. No. 33.46.10

| Abbreviation | Chemical Description (Supplier, Location) |
|---|---|
| Polymerizable Monomer | |
| UDMA | Diurethane Dimethacrylate CAS #72869-86-4 2-Propenoic acid, 2-methyl-, 7,7,9 (or 7,9,9) trimethyl-4,13-dioxo 3,14-dioxa-5,12-diazahexadecane-1,16-diyl ester, available from Dajac Laboratories |
| TEGDMA | triethyleneglycol dimethacrylate |
| Inorganic Filler | |
| Nano-Cluster | Refers to silane-treated zirconia/silica nanocluster filler prepared essentially as described in U.S. Pat. No. 6,730,156 (Preparatory Example A (line 51-64) and Example B (column 25 line 65 through column 26 line 40). |
| 20 nm Si Nanomer | Refers to silane-treated nano-sized silica having a nominal particle size of approximately 20 nanometers, prepared essentially as described in U.S. Pat. No. 6,572,693 B1, (column 21, lines 63-67 for Nanosized particle filler, Type #2. |
| Components of Photoinitiator Package | |
| BHT | 2,6-di-tert-butyl-4-methylphenol (Sigma-Aldrich Fine Chemicals, St. Louis, MO) |
| CPQ | camphorquinone (Sigma-Aldrich) |
| DPIHFP | "DPIHFP" refers to diphenyl iodonium hexafluorophosphate; |
| EDMAB | ethyl 4-(N,N-dimethylamino)benzoate (Sigma-Aldrich) |

Synthesis of Tri-HydroxyEthyl Iso Cyanurate Tris HEMA Phthalate (THEICTHP)

Phthalic acid anhydride (57.0 g, 0.385 mol, CAS #85-33-9, Alfa Aesar, lot G30T004), 4-(dimethylamino)pyridine (DMAP, 4.9 g, 0.04 mol, CAS #1122-58-3, Alfa Aesar, lot L125009), 2-hydroxyethylmethacrylate (HEMA, 50.9 g, 0.391 mol, and butylated hydroxytoluene (BHT, 0.140 g) were charged into a 2-liter 3-neck reaction flask equipped with a mechanical stirrer, a thermocouple connected to a temperature controller, a dry air stream running through a T-shape connection into the reactor then to an oil bubbler, and a heating mantle. With continuous stirring, the flask contents were heated to 95° C., by which all components dissolved and a clear liquid was obtained. Heating at 95° C. and stirring were continued for 5 hours. The heat was turned off and the flask contents were allowed to cool to room temperature while still being stirred under dry air. Acetone (250 ml) was added followed by tris-(2-hydroxyethyl)isocyanurate (33.58 g, 0.158 mol, from TCI). The heating mantle was replaced with an ice bath, where the mixture was cooled to 0-5° C. A solution made from dicyclohexyl carbodiimide (DCC, 81 g, 0.393 mol) in 120 ml acetone was placed into a 500 ml dropping funnel which was placed in-between the reaction flask and the dry air in-let. The DCC solution was added slowly to the continuously stirred reaction mixture in a rate where the reaction mixture temperature would not exceed 10° C. After complete addition of the DCC solution, the reaction was stirred in the ice bath for 2 hours in at room temperature overnight. On day 2, the solid formed was removed by vacuum filtration and the residue was concentrated in a rotary evaporator at 40-45° C. bath. The residue was dissolved in 300 ml solution of ethylacetate:hexanes, 2:1 by volume. The obtained solution was extracted with 200 ml of 1.0 N. HCl, 200 ml of 10% aqueous, 200 ml $H_2O$, and 200 ml brine. The organic layer was concentrated in a rotary evaporator with 40° C. bath. Further drying was done under a vacuum pump at 50° C. for 3 hours with air bleeding into the product during the whole time to give an almost colorless hazy viscous liquid.

Refractive index was measured and found to be 1.5386. By use of NMR the liquid was determined to be the product shown is the following reaction scheme. The calculated molecular weight of the depicted end product was determined to be 1041 g/mole. The calculated molecular weight of the linking group was determined to be 220 g/mole.

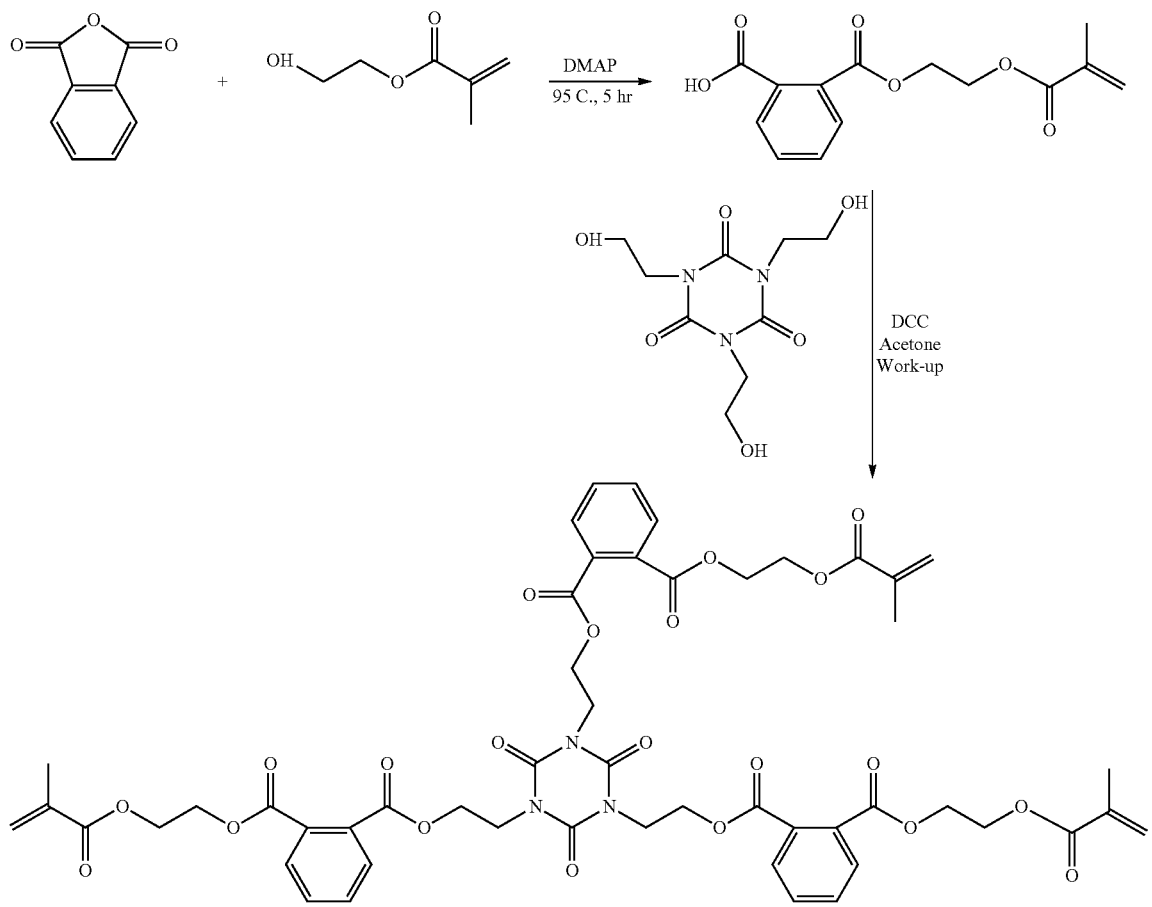

Synthesis of Tri-HydroxyEthyl Iso Cyanurate Di-HEMA Phthalate (THEICDHP)

THEICDHP was made from tris-(2-hydroxyethyl)isocyanurate (26.6 g, 0.10 mole) and 2 equivalents of mono-(2-methacryloxyethyl)phthalate (56.6 g, 0.20 mol) following the same procedure described for THEICTHP above. The product was isolated as a viscous liquid and structure was confirmed by NMR. The calculated molecular weight of the depicted end product was determined to be 781 g/mole. The calculated molecular weight of the linking group was determined to be 220 g/mole.

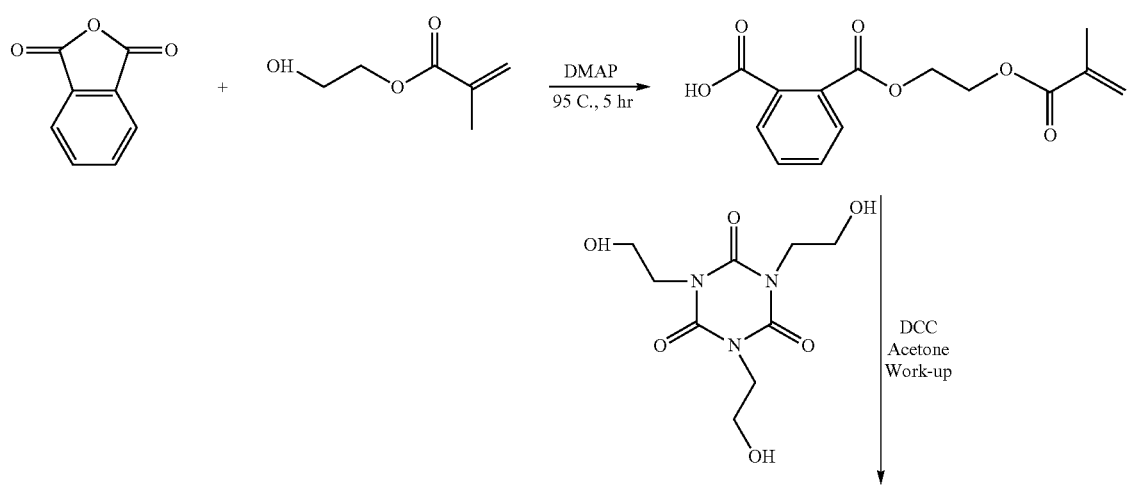

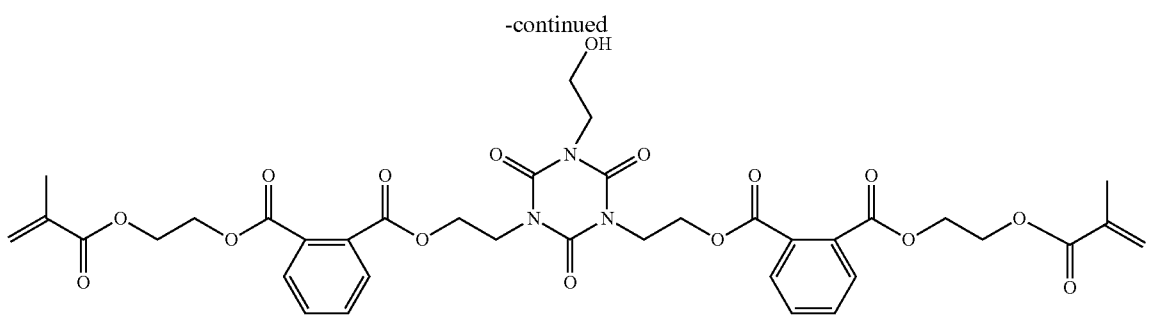

Synthesis of Tri-HydroxyEthyl Iso Cyanurate Di-HEMA Phthalate Octanoate(THEICDHPO)

THEICDHPO was made from tris-(2-hydroxyethyl)isocyanurate (50.20 g, 0.19 mole) and 2 equivalents of mono-(2-methacryloxyethyl)phthalate (106.6 g, 0.38 mol) and one equivalent octanoic acid (27.2 g, 0.19 mol) flowing the same procedure described for THEICTHP above. The product was isolated as a viscous liquid and structure was confirmed by NMR. The calculated molecular weight of the depicted end product was determined to be 907 g/mole. The calculated molecular weight of the linking group was determined to be 220 g/mole.

Preparation of THPICTHP

A sample of HEMA phthalate made according to the procedure described above for THEICTHP was purified from the DMAP catalyst by dissolving in ethylacetate/hexanes 2:1 then extracting with 1.N HCl then washing with water followed by brine. The acid was concentrated then used in making THPICTHP.

HEMA-phthalate (135 g, 0.486 mol) was charged into a 250 ml 3-neck flask equipped with a mechanical stirrer, a thermocouple connected to a temperature controller, a dry air stream running through a T-shape connection into the reactor then to an oil bubbler, and a heating mantle. Triphenylanti-

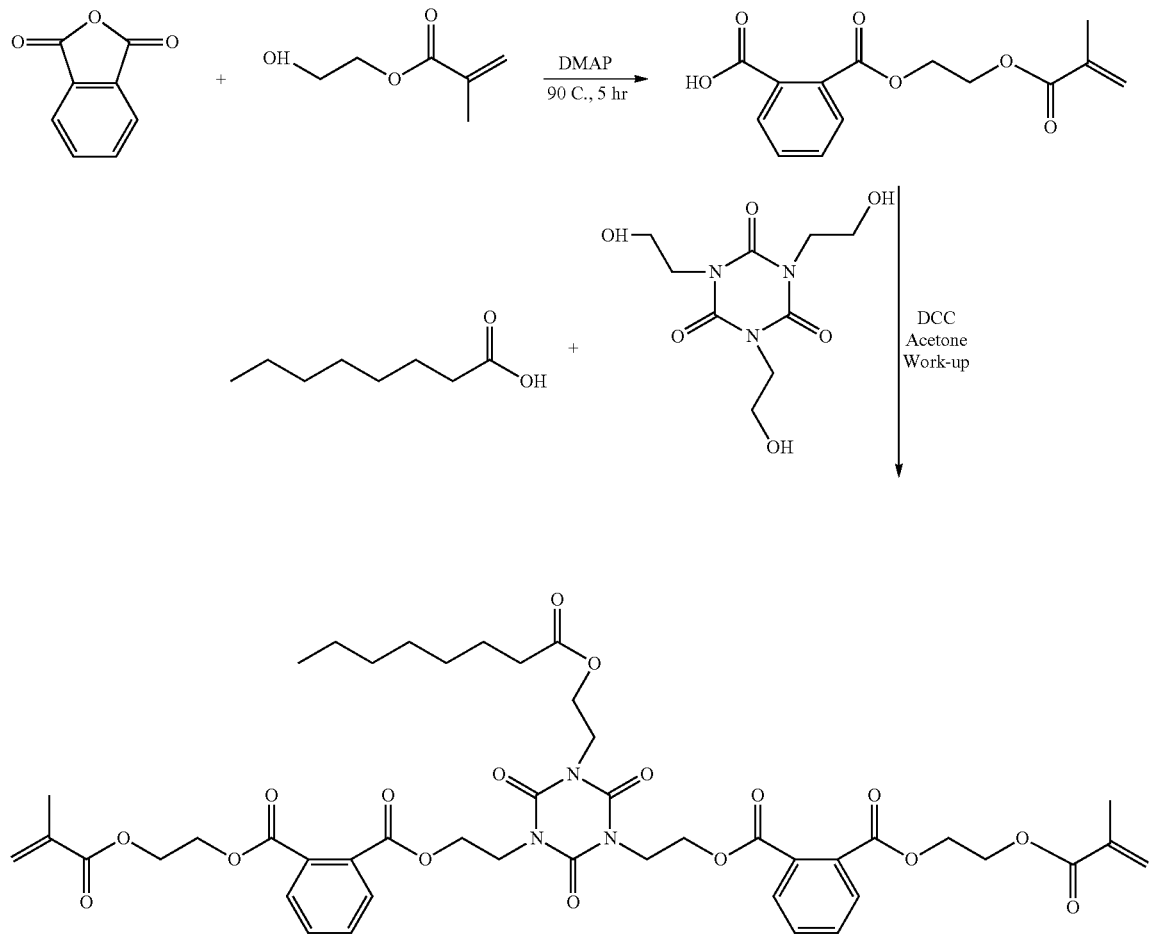

mony (1.4 g) was added and the mixture was heated to 100° C. Tris-epoxypropyl isocyanurate (57.15 g, 0.172 mol) was added in small increments over 1 hour. After complete addition, heating at 100 was resumed for 4 hours. Triphenylphosphine (0.360 g) was added and heating at 100 was continued for another 3 hours. The heat was turned off and the obtained viscous liquid was collected in quantitative yield.

Refractive index was measured and found to be 1.5365. By use of NMR the liquid was determined to be the product shown is the following reaction scheme. The calculated molecular weight of the depicted end product was determined to be 1131 g/mole. The calculated molecular weight of the linking group was determined to be 250 g/mole.

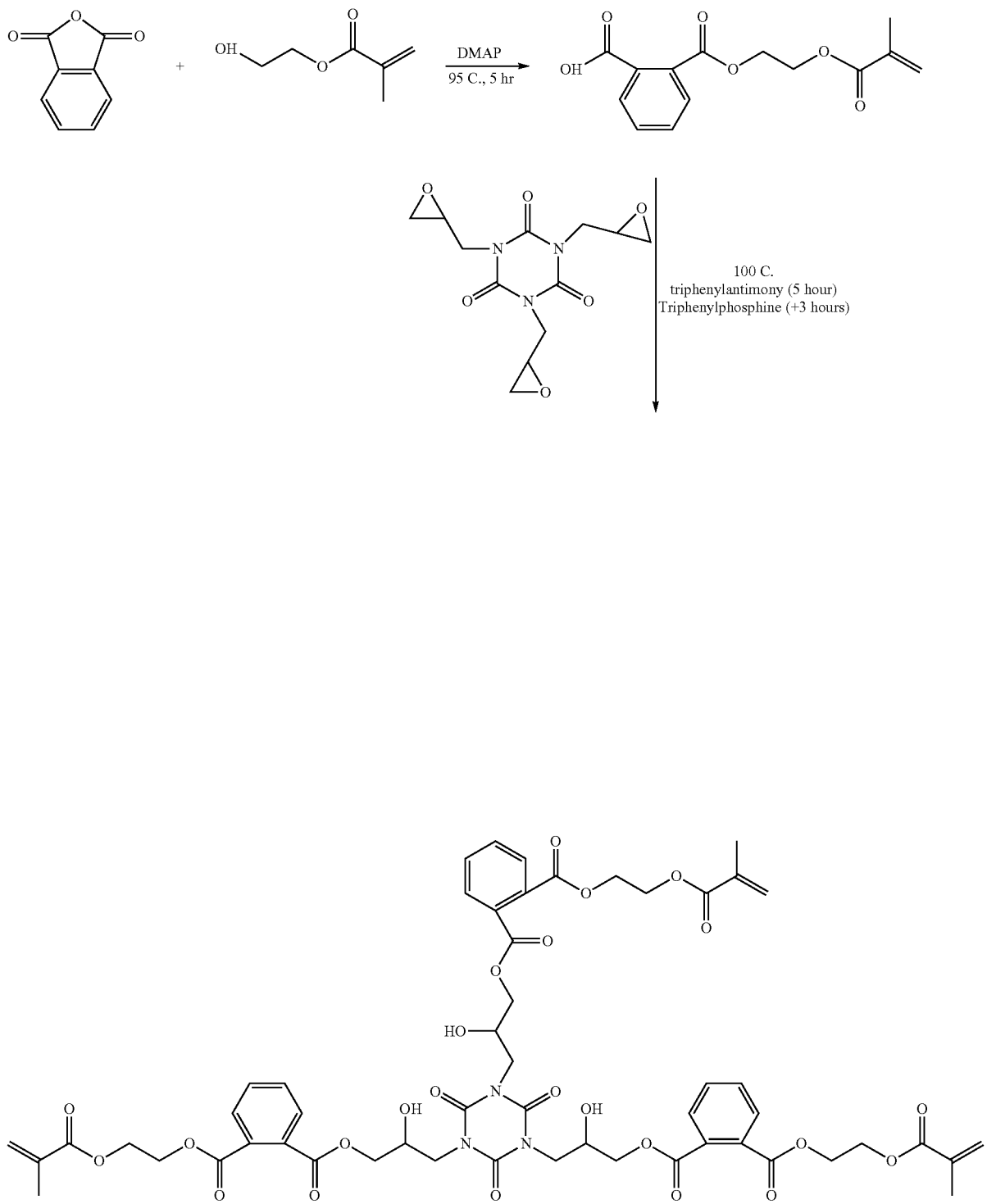

Preparation of THPICTHS

THPICTHS was prepared from trigylcidyl isocyanurate (34.4 g, 0.11 mol), and mono-(2-methacryloxyethyl)succinate (75.90 g, 0.33 mol, Aldrich Chemical) following the same procedure used for THPICTHP. The structure was confirmed by NMR. The calculated molecular weight of the depicted end product was determined to be 987 g/mole. The calculated molecular weight of the linking group was determined to be 202 g/mole.

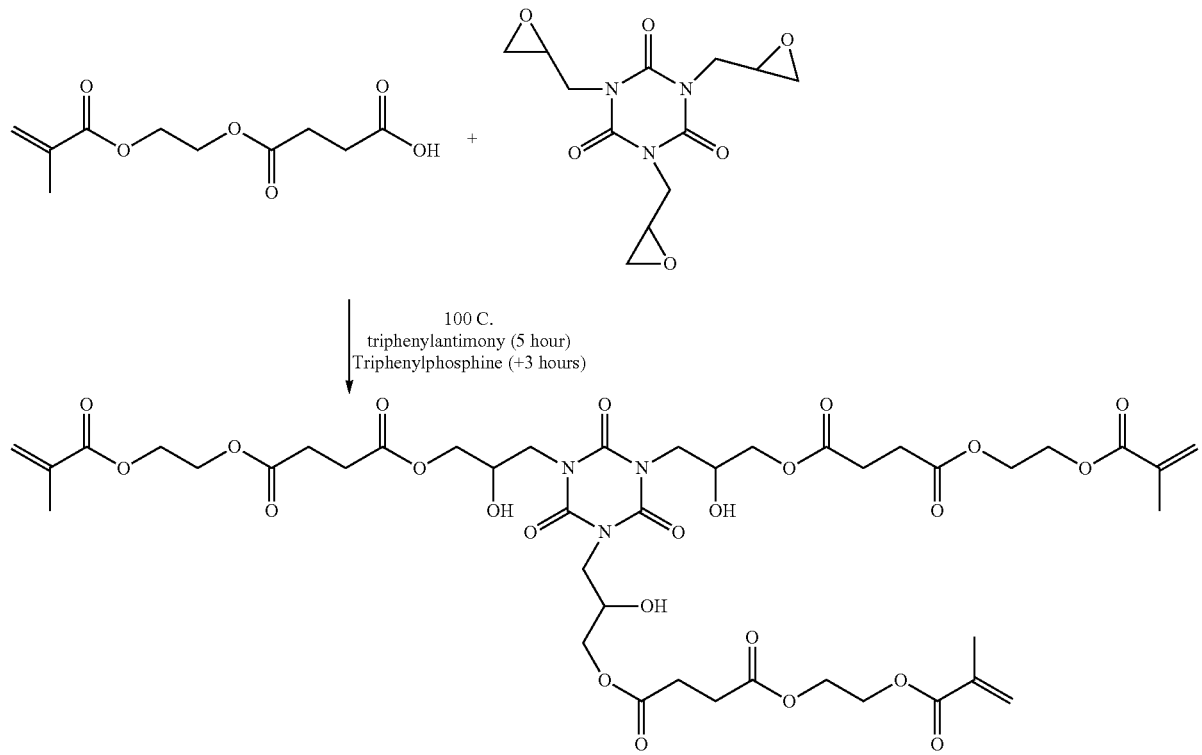

Preparation of THPICDHSB

THPICDHSB was prepared in a manner similar to that of THPICTHS using trigylcidyl isocyanurate (34.4 g, 0.114 mol), two equivalent mono-(2-methacryloxyethyl)succinate (50.22 g, 0.22 mol) and one equivalent benzoic acid (14.4 g, 0.11 mol). The structure was confirmed by NMR. The calculated molecular weight of the depicted end product was determined to be 879 g/mole. The calculated molecular weight of the linking group was determined to be 202 g/mole.

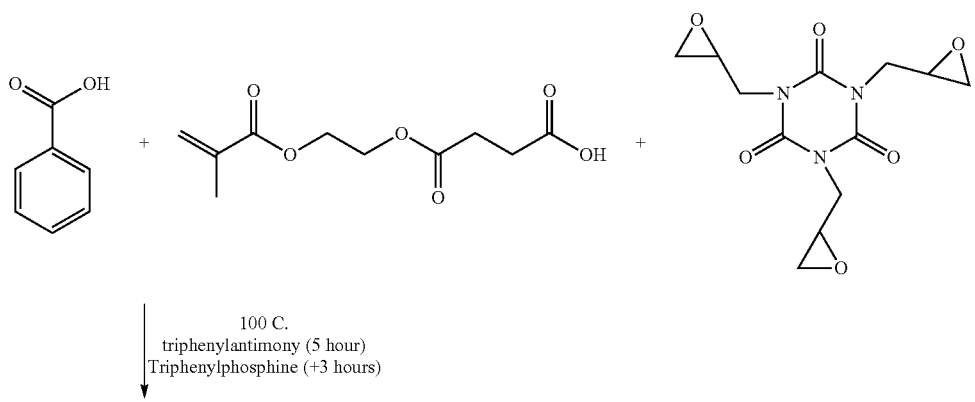

-continued

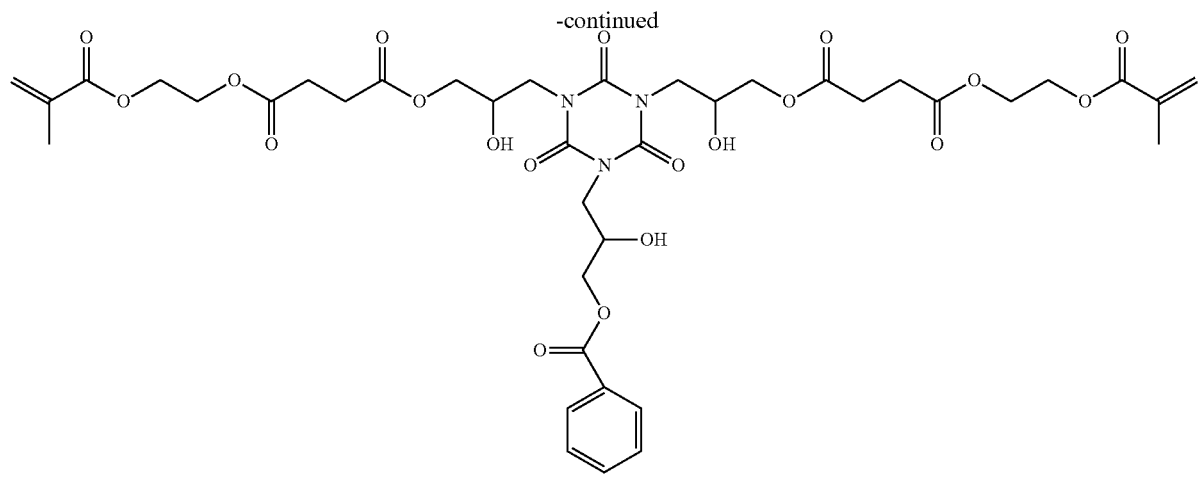

Synthesis of Mono(meth)acrylate Iscocyanurate
(Tri-hydroxyethyl isocyanurate mono-HEMA
phthalate di-octanoate)

Isocyanurates carrying one methacrylate functional group along with two non-functional alkyl or aryl groups are prepared by reacting three equivalents of tris-[2-hydroxyethyl] isocyanurate with two equivalents of non-functional aryl or alkyl carboxylic acid and one equivalent of a methacrylated carboxylic acid. The following is an example of a mono-methacrylated isocyanurate Phthalic acid anhydride (1 equivalent), 4-(dimethylamino) pyridine [DMAP, 0.1 equivalent], 2-hydroxyethylmethacrylate (HEMA, 1 equivalent), and butylated hydroxytoluene (BHT, 500 ppm) are charged into a 3-neck reaction flask equipped with a mechanical stirrer, a thermocouple connected to a temperature controller, a dry air stream running through a T-shape connection into the reactor then to an oil bubbler, and a heating mantle. With continuous stirring, the flask contents are heated to 95° C. for 5 hours. The heat is turned off and the flask contents are allowed to cool to room temperature while still being stirred under dry air. Acetone (700 ml per one equivalent of the isocyanurate) is added followed by octanoic acid (2 quivalent) and tris-(2-hydroxyethyl)isocyanurate (3 equivalent). The heating mantle is replaced with an ice bath, where the mixture is cooled to 0-5° C. A solution of dicyclohexyl carbodiimide (DCC, 3 equivalent) in 250 ml acetone per equivalent is placed into a dropping funnel which is placed in-between the reaction flask and the dry air in-let. The DCC solution is added slowly to the continuously stirred reaction mixture in a rate where the reaction mixture temperature would not exceed 10° C. After complete addition of the DCC solution, the reaction is stirred in the ice bath for 2 hours in at room temperature overnight. On day 2, the solid formed is removed by vacuum filtration and the residue is concentrated in a rotary evaporator at 40-45° C. bath. The residue is dissolved in a solution of ethylacetate:hexanes, 2:1 by volume (700 ml per equivalent of isocyanurate). The obtained solution is extracted with 1.0 N. HCl (1×500 ml per equivalent), 10% aqueous NaHCO3 (1×500 ml per equivalent), H₂O (1×500 ml per equivalent), and brine (1×500 ml per equivalent). The organic layer is concentrated in a rotary evaporator with 40° C. bath. Further drying is done under a vacuum pump at 50° C. for 3 hours with air bleeding into the product during the whole time to give an almost colorless hazy viscous liquid.

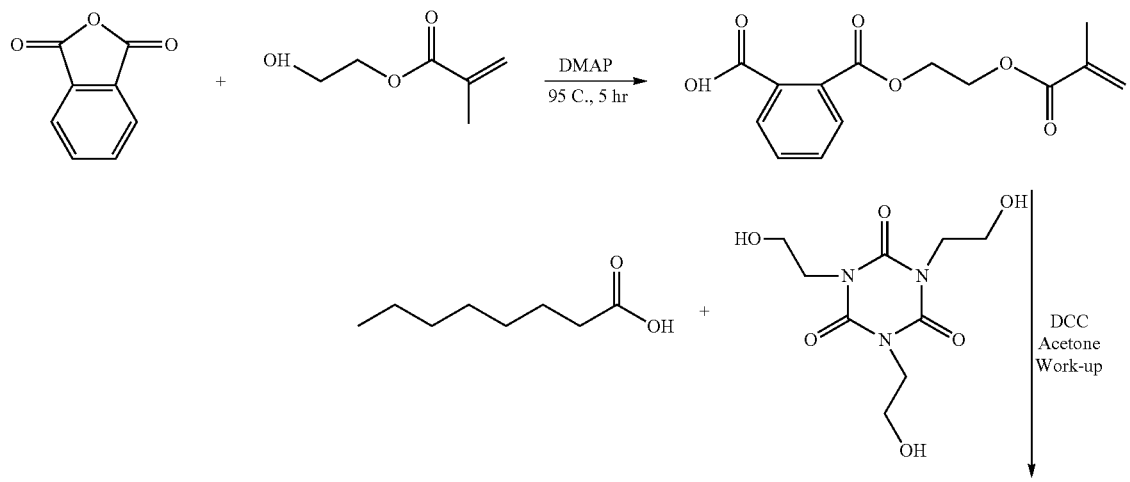

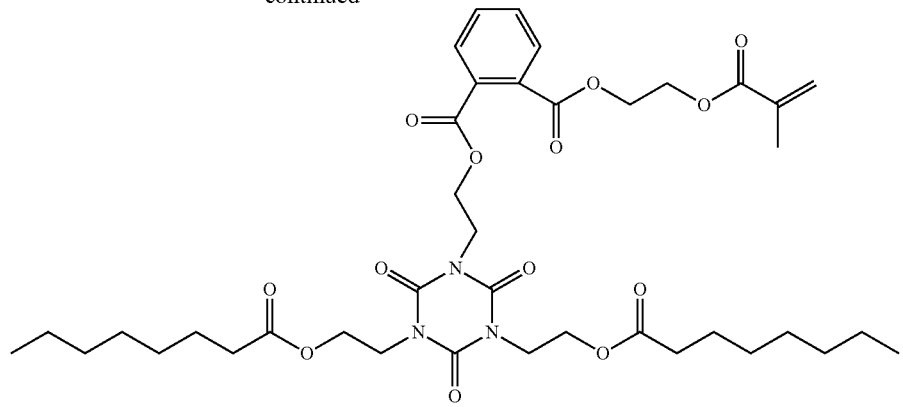

Tris(2-methacryloyloxyethoxy-5-methyl-hexa-hydrophthaloyloxyethyl) isocyanurate (t-HEMA-Hex-HPI)

2-Methyl-hexahydrophthalic anhydride (Also known as 4-methyl-1,2-cyclohexanedicarboxylic anhydride; 210.0 g, 1.25 mol, CAS #19438-60-9, Alfa Aesar, lot B04w039), 4-(dimethylamino)pyridine (DMAP, 7.5 g, 0.06 mol, CAS #1122-58-3, Alfa Aesar, lot L125009), 2-hydroxyethyl-methacrylate (HEMA, 162.5 g, 1.25 mol, and butylated hydroxytoluene (BHT, 0.380 g) were charged into a 1-liter 3-neck reaction flask equipped with a mechanical stirrer, a thermocouple connected to a temperature controller, a dry air stream running through a T-shape connection into the reactor then to an oil bubbler, and a heating mantle. The mixture was continuously stirred at 95° C. for 5 hours. The heat was turned off and the flask contents were allowed to cool to room temperature to give 4-methyl-(2-methacryloyloxyethyl) hexahydrophthalic acid intermediate as a colorless viscous liquid. Structure was confirmed by NMR.

In a separate 500 ml 3-neck flask equipped with a mechanical stirrer, a thermocouople connected to a temperature controller, and a dry air blanket was charged 4-methyl-(2-methacryloyloxyethyl)hexahydrophthalic (80.9 g, 0.271 mol) as solution in 200 mL ethylacetate. To the flask was then added tris-(2-hydroxyethyl)isocyanurate (22.35 g, 0.086 mol, from TCI) followed by DMAP (3.2 g, 0.03 mol, CAS #1122-58-3, Alfa Aesar, lot L125009). The flask was placed in an ice bath till flask contents temperature reached 0-5 C. With continuous stirring, was added a solution made from dicyclohexyl carbodiimide (DCC, 57 g, 0.277 mol) in 120 ml ethylacetate which was placed in a 500 ml dropping funnel placed on one of the flask side-arms. The DCC solution was added slowly to the continuously stirred reaction mixture in a rate where the reaction mixture temperature would not exceed 10° C. After complete addition of the DCC solution, the reaction was stirred in the ice bath for 2 hours in at room temperature overnight. On day 2, the solid formed was removed by vacuum filtration and the residue was concentrated in a rotary evaporator at 40-45° C. bath. The residue was dissolved in 300 ml solution of ethylacetate:hexanes, 2:1 by volume. The obtained solution was extracted with 200 ml of 1.0 N. HCl, 200 ml of 10% aqueous, 200 ml $H_2O$, and 200 ml brine. The organic layer was concentrated in a rotary evaporator with 40° C. bath. Further drying was done under a vacuum pump at 50° C. for 3 hours with air bleeding into the product during the whole time to give a colorless viscous liquid. Product's structure was confirmed by NMR and found to be consistent with the reaction scheme below. The calculated molecular weight of the depicted end product was determined to be 1100 g/mole.

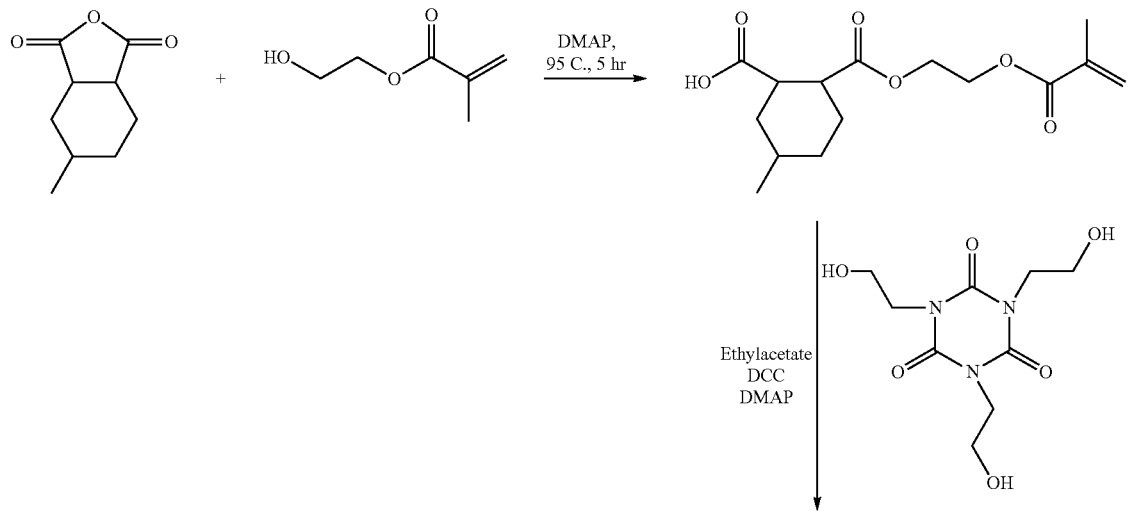

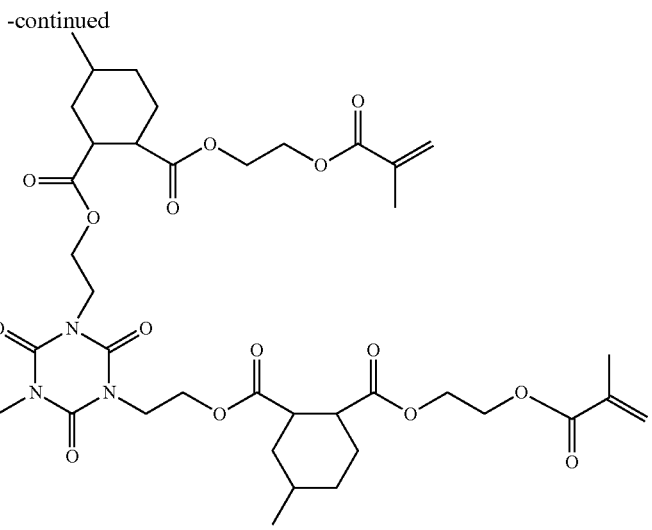

Tris(2-methacryloyloxyethoxy-5-methyl-hexa-hydrophthaloyloxyethyl) KarenzMT NR1 Derivative (Karenz NR1-TMA)

In a 500 ml 3-neck flask equipped with a mechanical stirrer, a thermocouople connected to a temperature controller, and a dry air blanket was charged 4-methyl-(2-methacryloyloxyethyl)hexahydrophthalic prepared in the previous step (65.03, 0.218 mol) as solution in 200 mL ethylacetate. To the flask was then added KarenzMT NR1 (40.0 g, 0.07 mol, Lot #791301, Showa Denko K.K., Kanagawa, Japan) followed by DMAP (2.6 g, 0.02 mol, CAS #1122-58-3, Alfa Aesar, lot L125009). The flask was placed in an ice bath till flask contents temperature reached 0-5 C. With continuous stirring, was added a solution made from dicyclohexyl carbodiimide (DCC, 44.5 g, 0.216 mol) in 120 ml ethylacetate which was placed in a 500 ml dropping funnel placed on one of the flask side-arms. The DCC solution was added slowly to the continuously stirred reaction mixture in a rate where the reaction mixture temperature would not exceed 10° C. After complete addition of the DCC solution, the reaction was stirred in the ice bath for 2 hours in at room temperature overnight. On day 2, the solid formed was removed by vacuum filtration and the residue was concentrated in a rotary evaporator at 40-45° C. bath. The residue was dissolved in 300 ml solution of ethylacetate:hexanes, 2:1 by volume. The obtained solution was extracted with 200 ml of 1.0 N. HCl, 200 ml of 10% aqueous, 200 ml $H_2O$, and 200 ml brine. The organic layer was concentrated in a rotary evaporator with 40° C. bath. Further drying was done under a vacuum pump at 50° C. for 3 hours with air bleeding into the product during the whole time to give a colorless viscous liquid with a slight haze. Product's structure was confirmed by NMR and found to be consistent with the reaction scheme below. The calculated molecular weight of the depicted end product was determined to be 1407.7 g/mole.

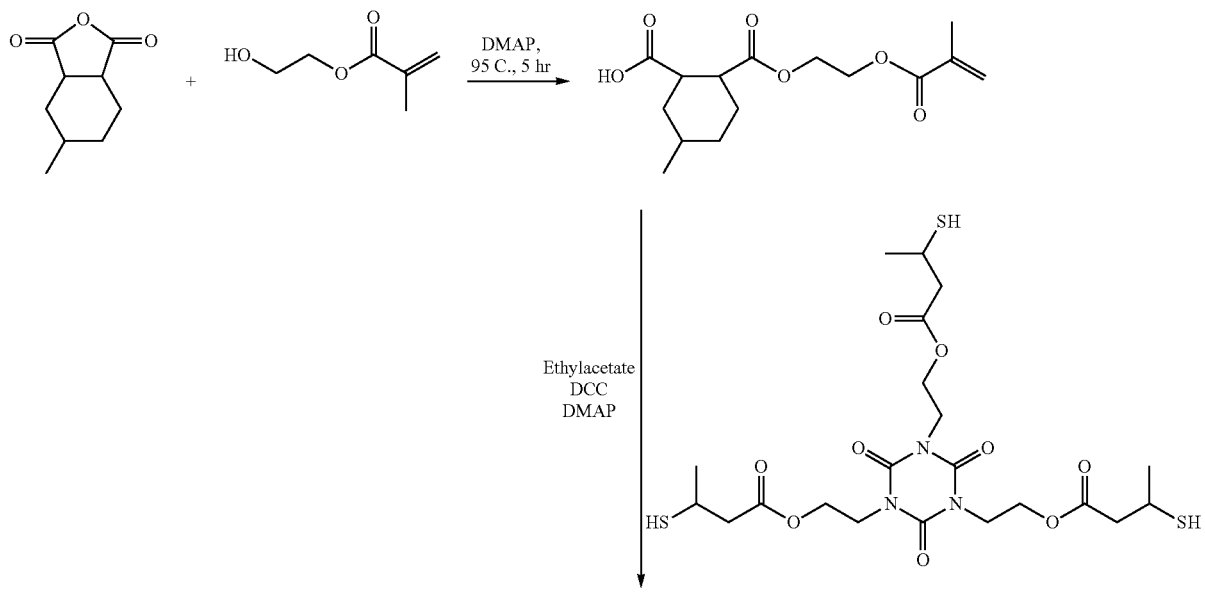

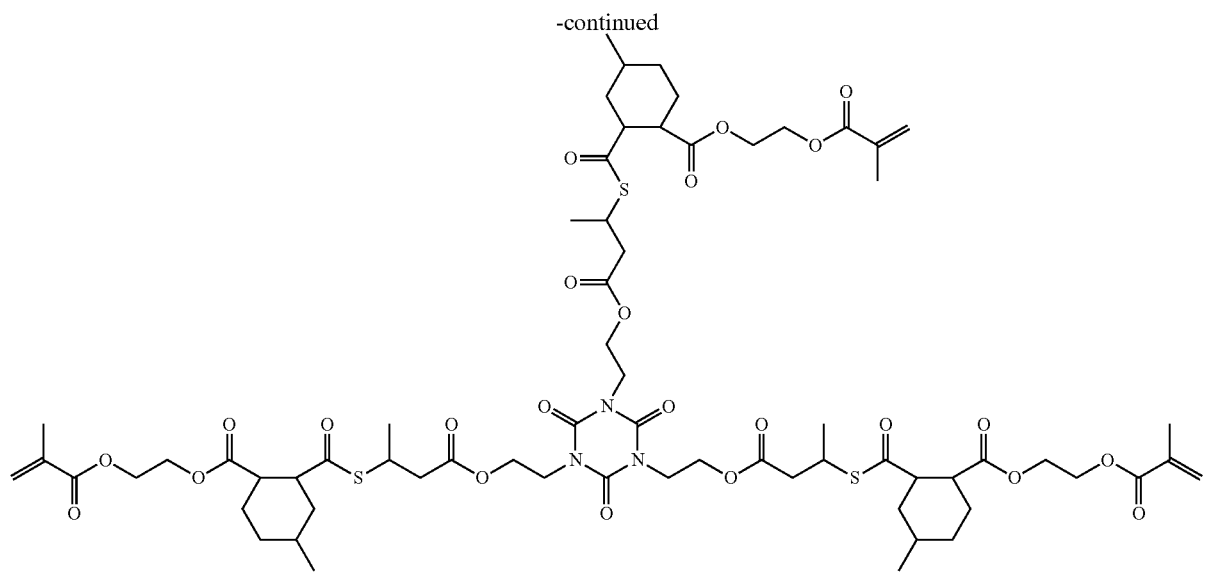

1-(2-Methacryloyloxyethyl)-2-(7-methylene-1,5-dithiaoctan-3-yl)phthalate (CAMP)

CAMP was made following the procedure disclosed in Abuelyaman et al WO 2006/122081 A1

Preparation of 1,2-Bis(2-Methacryloyloxyethyl)-4-(7-methylene-1,5-dithiaoctan-3-yl)trimellitate [TCAM-DiHEMA] (also described in Abuelyaman et al WO 2006/122081 A1)

Trimellitic acid (21.0 g, 0.10 mol TCI) was suspended in 200 ml of acetone in a 500 ml 3-neck flask equipped with a mechanical stirrer, a thermocouple connected to a temperature controller, a dry air stream running through a T-shape connection into the reactor then to an oil bubbler, and an ice bath. Then added were C-8 alcohol (17.6 g, 0.1 mol), HEMA (26.2 g, 0.2 mol), 4-(dimethylamino)pyridine (DMAP, 4 g, 0.03 mol, CAS #1122-58-3, Alfa Aesar, lot L125009) and BHT (60 mg). The mixture was cooled in the ice bath for 15-20 minutes (thermocouple reading was 0-5° C.). A solution of DCC (62.5 g, 0.303 mol) dissolved in 100 ml acetone was placed into a 500 ml dropping funnel which was placed in-between the reaction flask and the dry air in-let. The DCC solution was added drop-wise to the cold and vigorously stirred mixture in a manner that the temperature didn't exceed 10° C. After complete addition of the DCC solution, the flask was kept in the ice bath for 2 hours then at room temperature overnight.

On the second day, the solid formed was removed by filtration followed by concentrating the filtrate using a rotary evaporator. The residue was dissolved in 300 ml 2:1 ethylacetate:hexane then extracted with 100 ml of each of 1.0 N. HCl, 10% aqueous $NaHCO_3$, $H_2O$, and brine. The organic layer was dried by $Na_2SO_4$ then concentrated and dried using a rotary evaporator to give 57 g (96.6% yield) of a light yellow oil.

| Hardenable Dental Compositions Comprising Isocyanurate Multi(meth)acrylate Liquid Monomer | | | | |
|---|---|---|---|---|
| | Example 1 | Example 2 | Example 3 | Example 4 |
| THEICTHP | 54.95% | 54.95% | 58.87% | 58.87% |
| UDMA | 19.62% | 19.62% | 19.62% | 9.81% |
| TEGDMA | 3.92% | 3.92% | | |
| CAMP | 19.62% | | | |
| TCAM-DiHEMA | | 19.62% | 19.62% | 29.44% |
| CPQ | 0.23% | 0.23% | 0.23% | 0.23% |
| EDMAB | 1.00% | 1.00% | 1.00% | 1.00% |
| DPIHFP | 0.50% | 0.50% | 0.50% | 0.50% |
| BHT | 0.15% | 0.15% | 0.15% | 0.15% |
| 90.5 parts by weights NanoCluster/9.5 parts by weight 20 nm Si Nanomer | 74.00% | 74.00% | | |
| 91.5 parts by weights NanoCluster/8.5 parts by weight 20 nm Si Nanomer | | | 72% | 71% |

For each of the following experiments, the Control Dental Composite was a commercially available dental material comprising a comparable filler system and BisGMA as the primary monomer. A representative structure for BisGMA is depicted as follows:

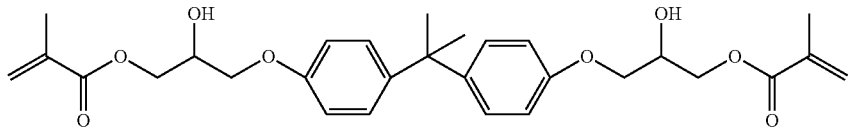 [SMILES: C=C(C)C(=O)OCC(O)COc1ccc(C(C)(C)c2ccc(OCC(O)COC(=O)C(=C)C)cc2)cc1]

| Watts Shrinkage | | | | | |
|---|---|---|---|---|---|
| | Example 1 | Example 2 | Example 3 | Example 4 | Control |
| Watts Shrinkage (%) | 1.83 | 1.81 | 1.59 | 1.39 | 1.99 |
| Standard Deviation | 0.02 | 0.03 | 0.04 | 0.04 | 0.03 |

| Diametral Tensile Strength (MPa) | | | | | | |
|---|---|---|---|---|---|---|
| | Example 1 | Example 2 | Control | Example 3 | Example 4 | Control |
| Diametral Tensile Strength (MPa) | 77.5 | 78.4 | 73.2 | 74.4 | 72.6 | 75.8 |
| Standard Deviation | 2.4 | 4.1 | 3.1 | 2.7 | 2.1 | 3.1 |

| Barcol Hardness | | | | | | |
|---|---|---|---|---|---|---|
| | Example 1 | Example 2 | Control | Example 3 | Example 4 | Control |
| Top | 78 | 77 | 81 | 77 | 74 | 81 |
| Top-Standard Deviation | 0.577 | 0.577 | 0.577 | 0.577 | 0.577 | 81 |
| Bottom | 80 | 80 | 82 | 77 | 75 | 73 |
| Bottom-Standard Deviation | 0.58 | 0.58 | 0.58 | 0.58 | 0.58 | 0 |

| Depth of cure (in mm) | | | | | |
|---|---|---|---|---|---|
| | Example 1 | Example 2 | Example 3 | Example 4 | Control |
| CL-2500[1] | 3.14 | 3.21 | 3.32 | 3.49 | 3.77 |
| CL 2500[1] standard deviation | 0.075 | 0.187 | 0.273 | 0.304 | 0.235 |
| FL2[2] | 3.72 | 3.76 | 4.03 | 3.81 | 3.99 |
| FL2[2]-standard deviation | 0.005 | 0.085 | 0.05 | 0.175 | 0.056 |

[1]3M Dental Products Curing Light 2500
[2]3M ESPE Elipar Free Light2

| Staining | | | | | |
|---|---|---|---|---|---|
| | Example 1 | Example 2 | Example 3 | Example 4 | Control |
| Coffee ΔE 1-Day | 8.0 | 7.3 | NT | NT | 12.5 |
| Coffee ΔE 3-Days | 10.9 | 9.8 | NT | NT | 15.9 |
| Coffee ΔE 7-Days | 12.4 | 12.0 | NT | NY | 17.7 |

NT—not tested

What is claimed is:

1. A hardenable dental composition comprising at least one isocyanurate monomer that is a liquid at about 25° C., the isocyanurate monomer comprising at least one terminal ethylenically unsaturated polymerizable group bonded to a nitrogen atom of a trivalent isocyanuric acid ring via a divalent linking group; wherein the divalent linking group is branched or comprises an aliphatic cyclic moiety or aromatic moiety; and comprises one or more moieties selected from ester, thioester, ether, thioether, and the divalent linking is free of urethane linkages.

2. The hardenable dental composition of claim 1 wherein the linking group has a molecular weight ranging from 100 g/mole to 500 g/mole.

3. The hardenable dental composition of claim 1 wherein the divalent linking group comprises an aromatic moiety and further comprises at least one hydroxyl moiety.

4. The hardenable dental composition of claim 1 wherein the ethylenically unsaturated polymerizable group is a (meth)acrylate group.

5. The hardenable dental composition of claim 1 wherein the monomer has a refractive index of at least 1.50.

6. The hardenable dental composition of claim 1 wherein the monomer has the general structure

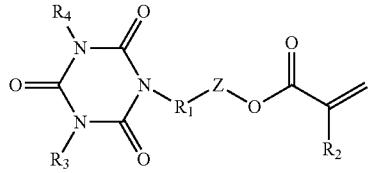

wherein
$R_1$ is alkylene, arylene, or alkarylene, optionally including a heteroatom;
$R_2$ is hydrogen or methyl;
Z is an alkylene, arylene, or alkarylene linking group comprising one or more moieties selected from ester, thioester, ether, thioether, and at least one Z comprises an aliphatic cyclic moiety or aromatic moiety; and
$R_3$ and $R_4$ are independently hydrogen, alkyl, aryl, or alkaryl, optionally including a heteroatom, or

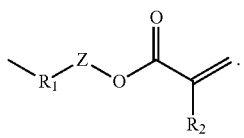

7. The hardenable composition of claim 6 wherein $R_1$ comprises no greater than 12 carbon atoms.

8. The hardenable dental composition of claim 6 wherein the monomer is a mono(meth)acrylate.

9. The hardenable dental composition of claim 8 wherein the dental composition further comprises a di(meth)acrylate isocyanurate monomer or tri(meth)acrylate isocyanurate monomer.

10. The hardenable dental composition of claim 8 wherein the dental composition further comprises a multi(meth)acrylate monomer that is not an isocyanurate monomer.

11. The hardenable dental composition of claim 6 wherein the monomer is a di(meth)acrylate or tri(meth)acrylate.

12. The hardenable dental composition of claim 11 wherein the monomer has the general structure

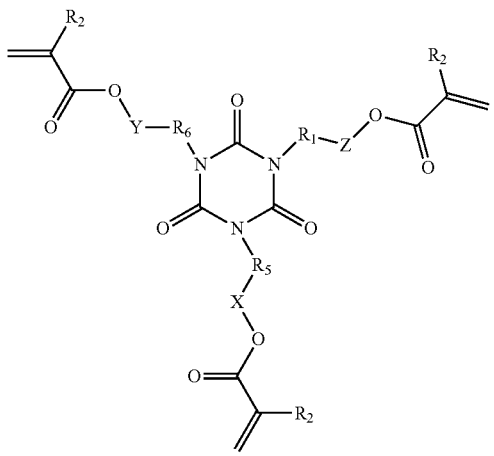

wherein
$R_1$, $R_5$, and $R_6$ are independently alkylene, arylene, or alkarylene, optionally including a heteroatom;
$R_2$ is hydrogen or methyl;
X, Y, and Z are independently an alkylene, arylene, or alkarylene linking group comprising one or more moieties selected from ester, thioester, ether, thioether, and combinations of said moieties and at least one of X, Y and Z comprises an aliphatic cyclic moiety or aromatic moiety.

13. The hardenable dental composition of claim 1 wherein the divalent linking group comprises an ester or thioester linkage.

14. The hardenable dental composition of claim 13 wherein the divalent linking group comprises an aliphatic or aromatic diester linkage.

15. The hardenable dental composition of claim 1 wherein the composition further comprises at least one filler comprising inorganic nanoparticles.

16. The hardenable dental composition of claim 15 wherein the inorganic nanoparticles are in the form of nanoclusters.

17. The hardenable dental composition of claim 15 wherein the inorganic nanoparticles comprise silica, zirconia, or mixtures thereof.

18. The hardenable dental composition of claim 15 wherein the isocyanurate monomer is a di(meth)acrylate or tri(meth)acrylate.

19. The hardenable dental composition of claim 18 wherein the composition further comprises a low volume shrinkage monomer selected from i) polymerizable compounds having at least one cyclic allylic sulfide moiety, ii) methylene dithiepane silanes, iii) oxetane silanes, or mixtures thereof.

20. The hardenable dental composition of claim 1 wherein the dental composition comprises at least one (meth)acrylate monomer selected from ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylglycol dimethacrylate (NPGDMA), polyethyleneglycol dimethacrylate (PEGDMMA), and mixtures thereof.

21. A dental article comprising the hardenable dental composition of claim 15 at least partially hardened.

22. The hardenable dental composition of claim 15 wherein the hardened composition exhibits a Watts Shrinkage of less than about 2%.

23. The hardenable dental composition of claim 15 wherein the hardened composition exhibits Diametral Tensile Strength is at least 75 MPa.

* * * * *